(12) United States Patent
Sum et al.

(10) Patent No.: US 6,498,170 B2
(45) Date of Patent: Dec. 24, 2002

(54) CYCLAMINE SULFONAMIDES AS β-3 ADRENERGIC RECEPTOR AGONISTS

(75) Inventors: Fuk-Wah Sum, Pomona; Baihua Hu, Nanuet, both of NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/904,158

(22) Filed: Jul. 12, 2001

(65) Prior Publication Data

US 2002/0022605 A1 Feb. 21, 2002

Related U.S. Application Data

(60) Provisional application No. 60/218,764, filed on Jul. 17, 2000.

(51) Int. Cl.$^7$ ............... A61K 31/445; A61K 31/4523; C07D 211/56

(52) U.S. Cl. ............ 514/329; 546/223; 546/200; 546/199; 546/198; 546/196; 546/21; 514/326; 514/322; 514/321; 514/320

(58) Field of Search ............... 514/329, 322, 514/321, 320, 326; 546/223, 200, 199, 198, 196, 21

(56) References Cited

U.S. PATENT DOCUMENTS

| 4,499,100 A | * 2/1985 | Kluge et al. ............... 514/321 |
| 5,561,142 A | 10/1996 | Fisher et al. |
| 5,578,620 A | 11/1996 | Fujita et al. |
| 5,614,523 A | 3/1997 | Audia et al. |
| 5,741,789 A | 4/1998 | Hibschman |
| 5,786,356 A | 7/1998 | Bell et al. |
| 5,789,402 A | 8/1998 | Audia et al. |
| 6,069,176 A | 5/2000 | Tsuchiya et al. |

FOREIGN PATENT DOCUMENTS

| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| EP | 0827746 A1 | 3/1998 |
| GB | 2163150 A | 2/1986 |
| WO | WO 99/65895 | 12/1999 |
| WO | WO 01/17989 A2 | 3/2001 |
| WO | WO 01/44227 A1 | 6/2001 |

OTHER PUBLICATIONS

Caroon, J.M. et al. : Antihypertensive 1–Acyl–4–[2–(1, 4–benzodioxan–2–yl)–2–hydroxyethylamino]piperidines. J. Pharmaceut. Sci. vol. 76, pp. 32–34, 1987.*

Marc S. Berridge et al., Nucl. Med. Biol., 1992, 563–569, 19(5).

Joan M Caroon et al., J. Pharm. Sci., Jan. 1987, 32–34, 76(1).

A. Guy et al., Synthesis, Sep. 1992, 821–22.

Manabu Hori et al., J. Org. Chem., 1998, 889–894, 63.

Yunsheng Huang et al., J. Med. Chem., 1998, 2361–2370, 41.

Bernard Hulin et al., J. Med. Chem., 1992, 1853–1864, 35.

Carl Kaiser et al., J. Med. Chem., 1977, 687–692, 20(5).

Yutaka Kawashima et al., Chem. Pharm. Bull, 1995, 1132–1136, 43(7).

Kiyoto Koguro et al., Synthesis, 1998, 910–914.

Gerard Leclerc et al., J. Med. Chem., 1980, 738–744, 23(7).

D. Mauleon et al., Il Farmaco,1989, 1109–1117, 44(11).

Alexander McKillop et al., J. Am. Chem. Soc., Sep. 1971, 4919–4920, 93(19).

Ricardo Tapia et al., Synthetic Communications, 1986, 681–687, 16(6).

Edward C. Taylor et al., Synthesis, Aug. 1981, 606–608.

Michiaki Tominaga et al., Chem. Pharm. Bull, 1987, 3699–3704, 35(9).

R.H. Uloth et al., J. Med. Chem., 1966, 88–97, 9.

Paul C. Unangst et al., J. Med. Chem., 1994, 322–328, 37.

Sophie Vanwetswinkel et al., J. Anitbiotics, Sep. 1994, 1041–1051, 47(9).

S. Tamada et al., JP 01061468 A2 (English abstract), 1989.

* cited by examiner

Primary Examiner—Charanjit S. Aulakh
(74) Attorney, Agent, or Firm—Michael R. Nagy

(57) ABSTRACT

This invention provides compounds of Formula I having the structure

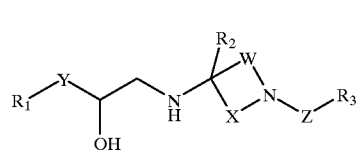

I wherein $R_1$, $R_2$, $R_3$, W, X, and Z are as defined hereinbefore or a pharmaceutically acceptable salt thereof, which are useful in treating metabolic disorders related to insulin resistance or hyperglycemia.

9 Claims, No Drawings

CYCLAMINE SULFONAMIDES AS β-3 ADRENERGIC RECEPTOR AGONISTS

This application claims the benefit of U.S. Provisional Application No. 60/218,764, filed Jul. 17, 2000.

BACKGROUND OF THE INVENTION

This invention relates to cyclylamine sulfonamide derivatives which are $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and and frequent urination, and are particularly useful in the treatment or inhibition of type II diabetes.

The subdivision of β adrenergic receptors (β-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agnoists, see: 1. A. D. Strosberg, *Annu. Rev. Pharmacol. Toxicol.* 1997, 37, 421; 2. A. E. Weber, *Ann. Rep. Med. Chem.* 1998, 33, 193; 3. C. P. Kordik and A. B. Reitz, *J. Med. Chem.* 1999, 42, 181; 4. C. Weyer, J. F. Gautier and E. Danforth, *Diabetes and Metabolism,* 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively.

Early developments in the $\beta_3$-agonist field are described in European patent 427480, U.S. Pat. Nos. 4,396,627, 4,478,849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436,257, and 5,578,620. These compounds were evaluated in Chinese hamster ovary (CHO) cells test procedures, expressing cloned human β3 receptors, which predict the effects that can be expected in humans (Granneman et al., *Mol Pharmacol.,* 1992, 42, 964; Emorine et al., *Science,* 1989, 245, 1118; Liggett *Mol. Pharmacol,* 1992, 42, 634).

$\beta_3$-Adrenergic agonists also are useful in controlling the frequent urge of urination. It has been known that relaxation of the bladder detrusor is under beta adrenergic control (Li JH, Yasay GD and Kau ST *Pharmacology* 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. Br. *J. Pharmacol.* 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

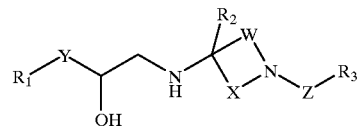

wherein:
W is $(CH_2)_m$;
X is $(CH_2)_n$;
Y is $OCH_2$, $SCH_2$, or a bond;
Z is $SO_2$, CO, or P(O)OR;
R is alkyl or aryl;
$R_1$ is phenyl substituted with $R_4$ and $R_5$, or Het substituted with $R_4$ and $R_5$;
$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;
$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —NHCOR$_7$, —NR$_8$R$_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylaikyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms $R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —NR$_8$R$_9$, or —NR$_9$(CH$_2$)$_p$—R$_8$ $R_8$ is hydrogen, alkoxy of 1–6 carbon atoms, alkyl of 1–6 carbon atoms, hydroxy, —(CH$_2$)$_p$—COR$_9$, or —(CH$_2$)$_p$—R$_9$;

$R_{10}$ is hydrogen, hydroxy, alkyl of 1–6 carbon atoms, alkoxy of 1–6 carbon atoms, or —NR$_{10}$R$_{10}$;

$R_{10}$ is hydrogen, alkyl of 1–6 carbon atoms, aryl, or Het;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

p is 0–6;

or a pharmaceutically acceptable salt thereof, which are selective agonists at human $β_3$ adrenergic receptors and are useful as antidiabetic, antihyperglycemic, and antiobesity agents.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

Alkyl includes both straight chain as well as branched moieties. By definition alkyl also includes alkyl moieties which are optionally mono- or poly substituted with groups such as halogen, hydroxy, cyano, alkoxy, aryloxy, arylalkyl, alkylthio, arylthio, amino, alkylamino, and dialkylamino. Halogen means bromine, chlorine, fluorine, and iodine.

Preferred aryl moieties include phenyl or naphthyl. Preferred Het moieties include: (a) 6-membered saturated, partially unsaturated, or unsaturated heterocycles containing 1–2 nitrogens, optionally fused to a phenyl ring; (b) 5-membered saturated, partially saturated, or unsaturated heterocycles containing 1–3 nitrogen, oxygen, or sulfur atoms, optionally fused to a phenyl ring; (c) saturated, partially unsaturated, or unsaturated bicyclic heterocycles containing 1–4 nitrogen, oxygen, or sulfur atoms; (d) carbazole, dibenzofuran, and dibenzothiophene. In the Het of categories (a), (b), and (c), ring carbon atoms may be carbonyl moieties, where the ring does not contain a double bond in that position (for example, thiazolidine-2,4-dione).

More preferred Het rings include pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, and isoquinoline. Particularly preferred Het include 1,3,-dihydrobenzoimidazol-2-one, benzo[1,2,5]thiadoazole, thiazoladine-2,4-dione, carbazole, dibenzofuran, and 2-oxo-2,3-dihydro-1H-benzoimidazole. It is understood that Het do not contain heteroatoms in arrangements which would make them inherently unstable. For example, the term Het does not include ring systems containing O—O bonds in the ring backbone.

The compounds of the present invention contain at least one asymmetric center. Additional asymmetric centers may exist on the molecule depending upon the structure of the substituents on the molecule. The compounds may be prepared as a racemic mixture and can be used as such, or may be resolved into the . In addition to covering the racemic compounds, this invention also covers all individual isomers, enantiomers, diasteromers or mixtures thereof, regardless of whether the structural representations of the compounds indicate such stereochemistry.

Preferred compounds of Formula I are those in which $R_2$ is hydrogen;

$R_3$ is alkyl of 1–6 carbon atoms, cycloalkyl of 4–8 carbon atoms, aryl substituted with $R_4$ and $R_5$, or Het substituted with $R_4$ and $R_5$;

$R_4$ and $R_5$ are each, independently, hydrogen, alkyl of 1–6 carbon atoms, halogen, alkoxy of 1–6 carbon atoms, arylalkoxy having 1–6 carbon atoms in the alkyl chain, hydroxy, arylalkyl having 1–6 carbon atoms in the alkyl chain, Het-alkyl having 1–6 carbon atoms in the alkyl chain, —NHCOR$_7$, —NHSO$_2$R$_7$, —NR$_8$R$_8$, or —COR$_8$;

Het is (a) a 6-membered saturated, partially unsaturated, or unsaturated heterocycle containing 1–2 nitrogens, optionally fused to a phenyl ring; (b) a 5-membered saturated, partially saturated, or unsaturated heterocycle containing 1–3 nitrogen, oxygen, or sulfur atoms, optionally fused to a phenyl ring; (c) a saturated, partially unsaturated, or unsaturated bicyclic heterocycle containing 1–4 nitrogen, oxygen, or sulfur atoms; (d) carbazole, dibenzofuran, and dibenzothiophene; wherein one or more of the ring carbon atoms of Het as described in (a), (b), or (c) may be a carbonyl moiety, where the ring does not contain a double bond in the position corresponding to that carbon atom;

or a pharmaceutically acceptable salt thereof.

More preferred compounds of Formula I are those in which

Y is OCH$_2$ or a bond;

Z is SO$_2$;

$R_2$ is hydrogen;

$R_3$ is phenyl substituted with $R_4$ and $R_5$, or Het substituted with $R_4$ and $R_5$;

$R_4$ and $R_5$ are each, independently, hydrogen, alkyl of 1–6 carbon atoms, alkoxy of 1–6 carbon atoms; arylalkyl having 1–6 carbon atoms in the alkyl chain, Het-alkyl having 1–6 carbon atoms in the alkyl chain, —NHCOR$_7$, —NHSO$_2$R$_7$, or —NR$_8$R$_8$;

$R_7$ is alkyl of 1–6 carbon atoms, —NR$_8$R$_9$, or —NR$_9$(CH$_2$)$_{p—R8}$;

$R_8$ is —(CH$_2$)$_p$—COR$_9$, or —(CH$_2$)$_p$—R$_9$;

$R_9$ is alkoxy of 1–6 carbon atoms or —NR$_{10}$R$_{10}$;

$R_{10}$ is hydrogen or alkyl of 1–6 carbon atoms;

Het is pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;

or a pharmaceutically acceptable salt thereof.

Specifically preferred compounds of this invention are:

a) 4-{(2S)-3-[1-(4-Butoxy-benzenesulfonyl)-azetidin-3-ylamino]-2-hydroxy-propoxy}-phenol;

b) 4-Butoxy-benzenesulfonic acid 4-{3-[1-(4-butoxy-benzenesulfonyl)-azetidin-3-ylamino]-2-hydroxy-propoxy}-phenyl ester;

c) 1-[1-(4-Butoxy-benzenesulfonyl)-azetidin-3-ylamino]-3-(9H-carbazol-4-yloxy)-propan-2-ol;

d) N-(5-{2-[1-(4-Butoxy-benzenesulfonyl)-azetidin-3-ylamino]-1-hydroxy-ethyl}-2-hydroxyphenyl)-methanesulfonamide;

e) [Butyl-(4-{3-[2-hydroxy-3-(4-hydroxy-phenoxy)-propylamino]-azetidine-1-sulfonyl}-phenyl)-amino]-acetic acid methyl ester;

f) {[4-(3-{Benzyl-[3-(4-benzyloxy-phenoxy)-2-hydroxy-propyl]-amino-azetidine-1-sulfonyl)-phenyl]-butyl-amino}-acetic acid methyl ester;

g) (2S)-1-[1-(4-Butoxy-benzenesulfonyl)-pyrrolidin-3-ylamino]-3-(9H-carbazol-4-yloxy)-propan-2-ol;

h) N-(5-{2-[1-(4-Butoxy-benzenesulfonyl)-pyrrolidin-3-ylamino]-1-hydroxy-ethyl}-2-hydroxy-phenyl)-methanesulfonamide;

i) 4-{(2S)-3-[1-(Benzo[1,2,5]thiadiazole-4-sulfonyl)-piperidin-4-ylamino]-2-hydroxy-propoxy}-1,3-dihydro-benzoimidazol-2-one;

j) (2S)-1-(4-Benzyloxy-phenoxy)-3-[1-(4-methoxy-benzenesulfonyl)-piperidin-4-ylamino]-propan-2-ol;

k) (2S)-1-(4-Benzyloxy-phenoxy)-3-[1-(4-butoxy-benzenesulfonyl)-piperidin-4-ylamino]-propan-2-ol;

l) 4-{3-[1-(4-Butoxy-benzenesulfonyl)-piperidin-4-ylamino]-2-hydroxy-propoxy}-phenol;

m) 4-{(2S)-2-Hydroxy-3-[1-(4-methoxy-benzenesulfonyl)-piperidin-4-ylamino]-propoxy}-phenol;

n) 4-{(2S)-2-Hydroxy-3-[1-(4-methoxy-benzenesulfonyl)-piperidin-4-ylamino]-propoxy}-1,3-dihydro-benzoimidazol-2-one;

o) (2S)-1-(9H-Carbazol-4-yloxy)-3-[1-(4-methoxy-benzenesulfonyl)-piperidin-4-ylamino]-propan-2-ol;

p) (2S)-1-[-(4-Butoxy-benzenesulfonyl)-piperidin-4-ylamino]-3-(9H-carbazol-4-yloxy)-propan-2-ol;

q) (2S)-1-(9H-Carbazol-4-yloxy)-3-{1-[4-(1,1-dimethyl-propyl)-benzenesulfonyl]-piperidin-4-ylamino}-propan-2-ol;

r) 3-{1-Hydroxy-2-[1-(4-methoxy-benzenesulfonyl)-piperidin-4-ylamino]-ethyl}-phenol;

s) 3-{2-[1-(4-Butoxy-benzenesulfonyl)-piperidin-4-ylamino]-1-hydroxy-ethyl}-phenol;

t) 3-(2-(1-[4-(1,1-Dimethyl-propyl)-benzenesulfonyl]-piperidin-4-ylamino}-1-hydroxy-ethyl)-phenol;

u) (2S)-1-(9H-Carbazol-4-yloxy)-3-[1-(3,4-dimethoxy-benzenesulfonyl)-piperidin-4-ylamino]-propan-2-ol;

v) 4-{(2S)-3-[1-(3,4-Dimethoxy-benzenesulfonyl)-piperidin-4-ylamino]-2-hydroxy-propox}-1,3-dihydro-benzoimidazol-2-one;

w) 5-(4-{4-[2-Hydroxy-3-(2-oxo-2,3-dihydro-1H-benzoimidazol-4-yloxy)-propylamino]-piperidine-1-sulfonyl}-benzyl)-thiazolidine-2,4-dione;

x) N-[5-(2-{1-[4-(2,4-Dioxo-thiazolidin-5-ylmethyl)-benzenesulfonyl]-piperidin-4-ylamino}-1-hydroxy-ethyl}-2-hydroxy-phenyl]-methanesulfonamid;

y) 4-{3-[1-(Dibenzofuran-2-sulfonyl)-piperidin-4-ylamino]-2-hydroxy-propoxy-1,3-dihydro-benzoimidazol-2-one;

z) N-(5-{2-[1-(Dibenzofuran-2-sulfonyl)-piperidin-4-ylamino]-1-hydroxy-ethyl}-2-hydroxy-phenyl)-methanesulfonamide;

aa) 1-Hexyl-3-(4-{4-[(2S)-2-hydroxy-3-(4-hydroxy-phenoxy)-propylamino]-piperidine-1-sulfonyl}-phenyl)-urea;

bb) 1-Hexyl-3-(4-{4-[2-hydroxy-3-(2-oxo-2,3-dihydro-1H-benzoimidazol-4-yloxy)-propylamino]-piperidine-1-sulfonyl}-phenyl)-urea;

cc) N-[5-(2-{1-[4-(3-Hexyl-ureido)-benzenesulfonyl]-piperidin-4-ylamino}-1-hydroxy-ethyl)-2-hydroxy-phenyl]-methanesulfonamide;

or a pharmaceutically acceptable salt thereof.

The compounds of this invention were be prepared according to the following schemes from commercially available starting materials or starting materials which can be prepared using literature procedures. These schemes show the preparation of representative compounds of this invention.

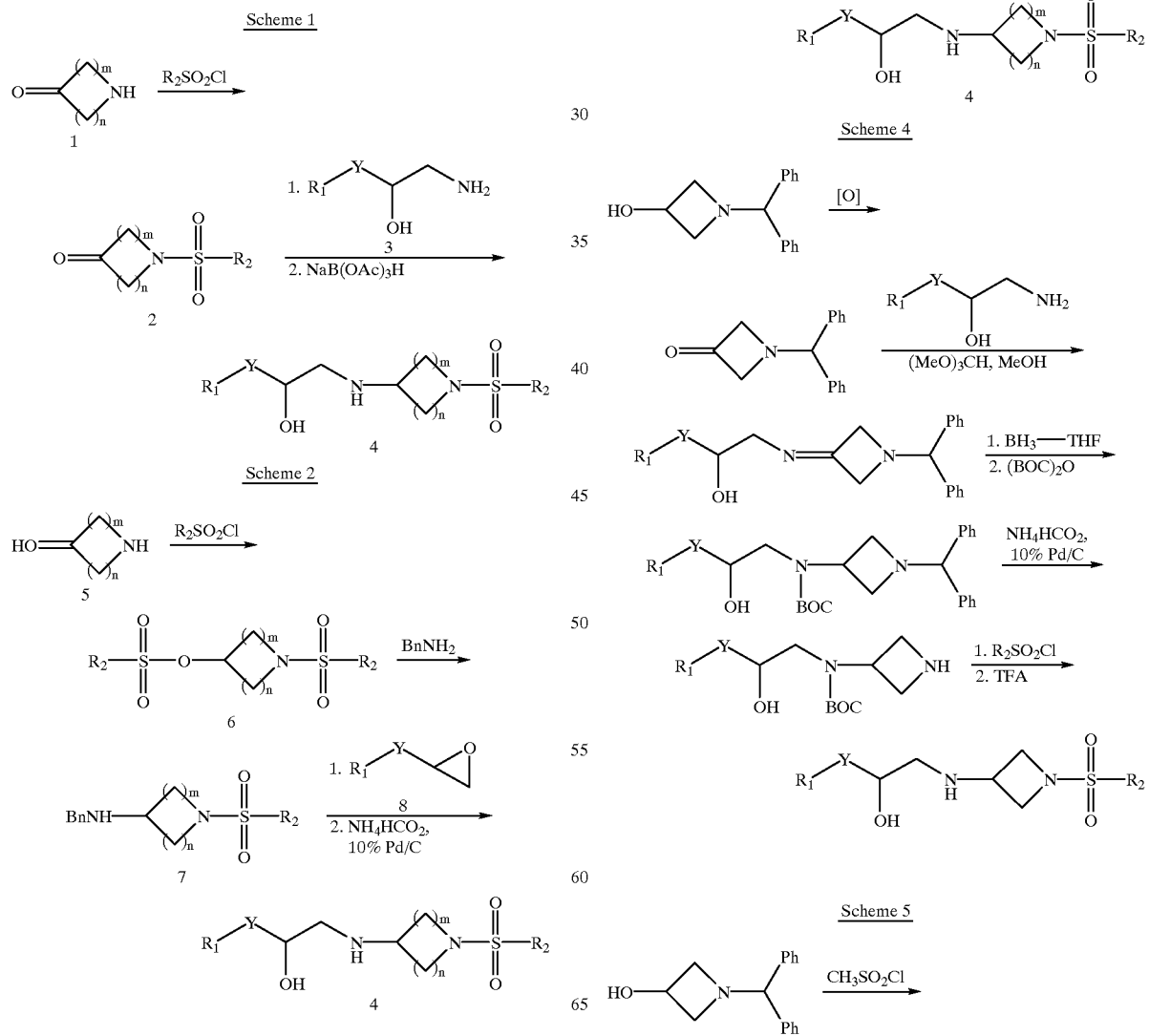

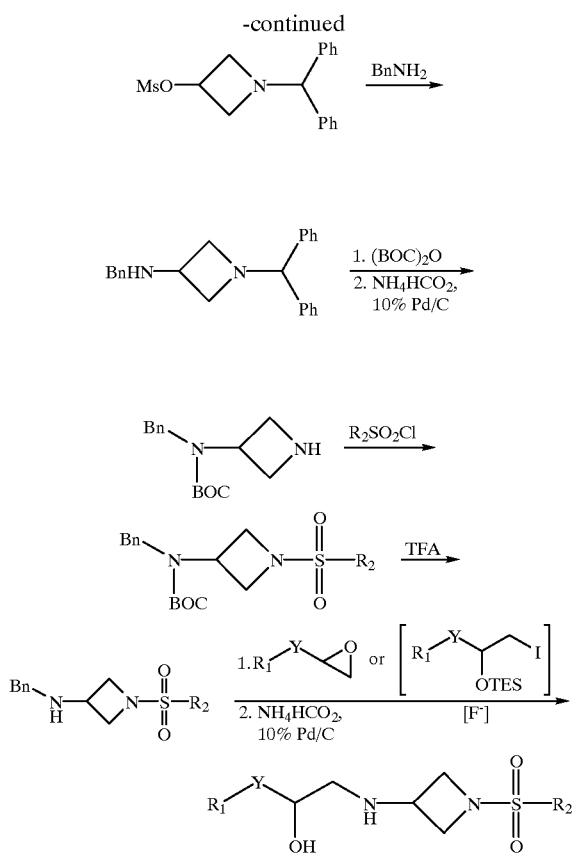

As shown in Scheme 1, reaction of an oxo-cyclylamine 1 (e.g. 4-piperidone, m=n=2) with a sulfonyl chloride gives the sulfonamide 2 which upon reductive amination with the appropriate ethanolamines 3 gives compound 4 which is a beta-3 adrenergic receptor agonist. A second synthetic route (Scheme 2) involves the di-sulfonylation of a hydroxy-cyclylamine 5, followed by sequential reactions with benzylamine, and oxirane 8, and then hydrogenation to yield the final product. A similar synthesis employing an N-sulfonylation and O-mesylation sequence is shown in Scheme 3. Azetidine derivatives are prepared from 1-(diphenylmethyl)-3-azetidine according to one of the synthetic routes shown in Scheme 4 and Scheme 5.

Many of the aryloxypropanolamines and arylethanolamines used in the above Schemes are commerically available or readily prepared by known methods [e.g., 1. A. Guy, Synthesis, 1992, 821; 2. A. A. Asselin, J. Med. Chem., 1986, 1009; 3. M. S. Berridge et al., Nucl. Med. Biol., 19, 1992, 563; 4. C. D. Jesudason, et al., EP0764640; 5. EP0659737.]. In one method (Scheme 6), equimolar amounts of a substituted phenol and (2S) or (2R)-glycidyl 3-nitrobenzenesulfonate are dissolved in an organic solvent such as acetone or dimethylformamide and treated with a base such as sodium hydride or potassium carbonate for 0.5 to 24 hours at temperatures of 20 to 100° C. to provide the corresponding aryloxyoxiranes. The aryloxyoxiranes are converted to the ethanolamines by regioselective ring opening of the oxirane with lithium azide in a solvent such as hexamethylphosphoramide, followed by reduction with triphenylphosphine or hydrogenation with 10% Pd/C as catalyst. Alternatively, the aryloxyoxiranes can be converted to the ethanolamines by regioselective ring opening of the oxirane with dibenzylamine, followed by hydrogenation with 10% Pd/C as catalyst.

Scheme 6

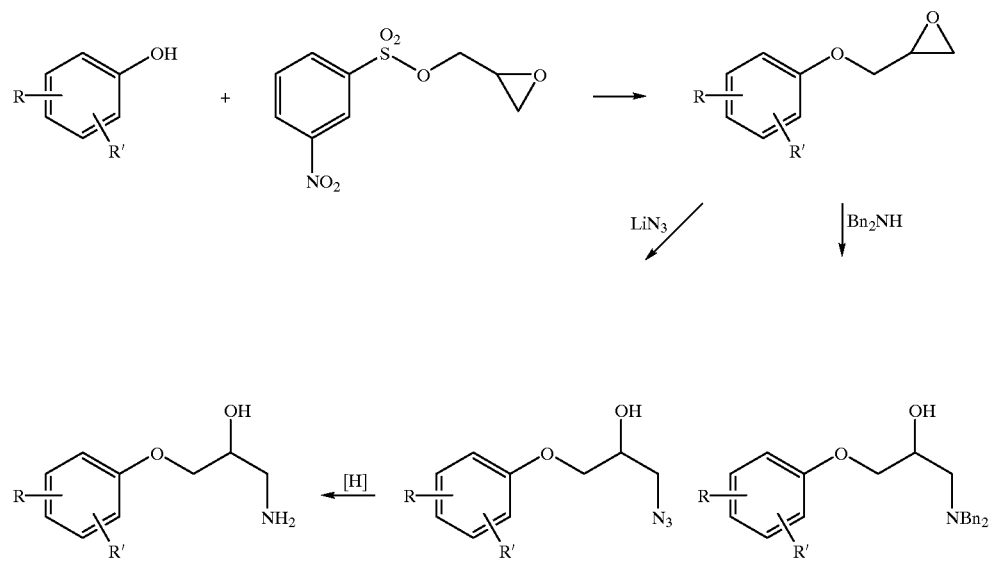

The arylethanolamines used in Schemes 1 and 4 can be prepared according to the methods shown in Scheme 7. Arylmethylketones are converted to the corresponding α-haloketones using known methods [J. March, Advanced Organic Chemistry, 3rd Ed., John Wiley and Sons, New York:1985, p529 and references cited therein]. The haloketones are reduced to the corresponding alcohol which can be protected as the triethylsilyl ether, or converted directly to the ethanolamine by treatment with ammonia or sodium azide followed by reduction. Treatment of the halo silyl ether with benzylamine followed by desilylation and hydrogenation also gives the corresponding arylethanolamine.

Scheme 7

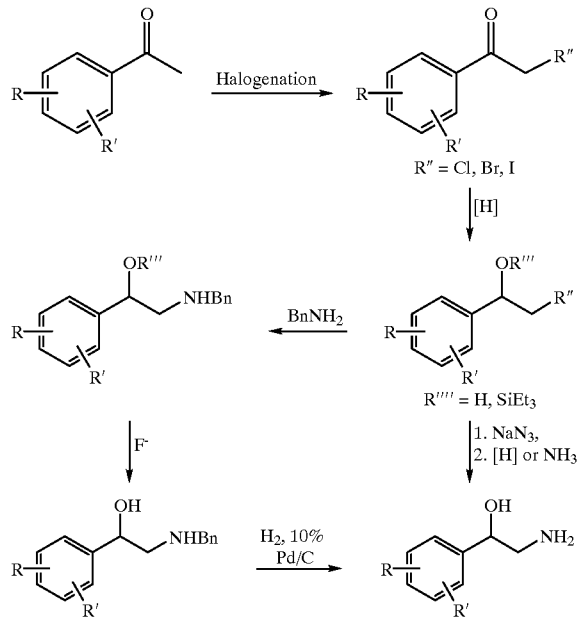

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., , *Eur. J. Biochem.*, 196:357–361 (1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and anti-sense primer 5'CTGGCGCCCAACGGCCAGTGGC-CAGTC3'; a NarI-AccI fragment, 5'TTGGCGCTGATGGC-CACTGGCCGTTTG3' as sense and 5'GCGCGTAGACGAAGAGCATCACGAG3' as anti-sense primer; an AccI-StyI fragment, sense primer 5'CTCGTGAT-GCTCTTCGTCTCACGCGC3' and anti-sense primer 5'GTGAAGGTGCCCATGATGAGACCCAAGG3' and a StyI-TAG fragment, with sense primer 5'CCCTGTGCAC-CTTGGGTCTCATCATGG3' and anti-sense primer 5'CCTCTGCCCCGGTTACCTACCC3'. The corresponding primer sequences are described in Mantzoros, C. S., etal., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$ _AR are prepared with the $\beta_3$-βARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoproternol at $10^{-5}$ M from the following formula:

$$IA = \frac{\% \text{ activity compound}}{\% \text{ activity isoproterenol}}$$

The following table shows the $EC_{50}$ and IA values for the representative compounds of this invention that were evaluated in this standard pharmacological test procedure that measured binding selectivity at that β-adrenergic receptors.

| Example | beta-3<br>IC$_{50}$ $\mu$M (IA) | beta-2<br>EC$_{50}$ $\mu$M(IA) | beta-1<br>EC$_{50}$ $\mu$M (IA) |
| --- | --- | --- | --- |
| 1 | 0.03 (0.82) | 0.9 (0.39) | 1.6 (0.49) |
| 5 | 78% at 10 $\mu$M | | |
| 8 | 0.8 (0.75) | | |
| 9 | 0.5 (0.8) | | |
| 14 | 0.85 (0.74) | (0.07) | (0.04) |
| 15 | 0.06 (0.88) | (0.03) | (0.1) |
| 20 | 0.08 (0.87) | (0.01) | (0.3) |
| 21 | 0.02 (1.2) | (0.02) | (0.1) |
| 23 | 0.1 (0.88) | | |

Based on the results obtained in these standard pharmacological test procedures, representative compounds of this invention have been shown to be selective $\beta_3$ adrenergic receptor agonists and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. For treating treating metabolic disorders related to insulin resistance or hyperglycemia generally satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum,, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following procedures describe the preparation of representative aryloxypropanolamines and arylethanolamines used in the preparation of compounds of this invention.

(1R)-2-Amino-1-(3-chloro-phenyl)-ethanol:

Lithium azide (7.5 g, 150 mmol) was added to a solution of (1R)-1-(3-chloro-phenyl)oxirane (15.5 g, 100 mmol) in hexamethylphosphoramide (70 mL). After being stirred at room temperature for 16 hours the suspension was poured into ice-water and the mixture was extracted with diethyl ether. The combined extracts were dried ($MgSO_4$) and concentrated. The residue was dissolved in 550 mL of $THF/H_2O$ (10:1) and triphenylphosphine (30 g, 114 mmol) was added. After overnight stirring at room temperature, the solvents were removed and the residue was purified by column chromatography on silica gel using triethylamine-methanol-methylene chloride (1:1:8) as the eluent to give the title compound as a free base. The free base was then dissolved in diethyl ether and slowly treated with HCl gas. The precipitate was collected by filtration to yield 15 g (72%) of the title compound as a white powder; $^1$H NMR (300 MHz, DMSO-d6) δ 2.83 (dd, J=12.8, 9.5 Hz, 1 H), 3.06 (dd, J=12.8, 3.2 Hz, 1 H), 4.80–4.90 (m, 1 H), 6.22 (d, J=4.0 Hz, 1 H), 7.10–7.75 (m, 4 H), 8.08 (brs, 2 ); MS (ES) mz: 171.7, 173.7 ($M^+$+H); HRMS Calcd. for $C_8H_{10}ClNO(M^+)$: 172.0529. Found: 172.0531.

(2S)-1-Amino-3-(4-benzyloxy-phenoxy)-propan-2-ol:

The title compound was prepared from (2S)-2-(4-benzyloxy-phenoxymethyl-oxirane (EP 0 714 883) according to the procedure described above as a white solid; $^1$H NMR (300 MHz, $CDCl_3$) δ 2.50–2.70 (m, 2 H), 3.33 (brs, 2 H), 3.60–3.90 (m, 3 H), 5.02 (s, 2 H), 6.90 (d, J=6.7 Hz, 2 H), 6.93 (d, J=6.7 Hz, 2 H), 7.25–7.50 (m, 5 H); MS (ES) m/z: 274.1 ($M^+$+H); HRMS Calcd. for $C_{16}H_{19}NO_3(M^+)$: 273.1365. Found: 273.1347. Anal. Calcd. for $C_{16}H_{19}NO_3$: C, 70.31; H, 7.01; N, 5.12. Found: C, 70.39; H, 6.80; N, 5.23.

(2S)-1-Amino-3-(4-hydroxy-phenoxy)-propan-2-ol:

A mixture of (2S)-1-amino-3-(4-benzyloxy-phenoxy)-propan-2-ol (0.9 g, 3.3 mmol) 0.2 mL of acetic acid and 10% Pd/C (0.3 g) in 70 mL of ethanol was pressurized with 20 psi hydrogen and shaken over 2 hours. The catalyst was then removed by filtering through a short pad of silica gel and the solvent was removed to give the title compound as an off-white solid; $^1$H NMR (300 MHz, DMSO-$d_6$) δ 1.86 (s, 1 H), 2.66 (dd, J=12.8, 5.3 Hz, 1H), 2.85 (dd, J=12.8, 3.5 Hz, 1H), 3.79–3.95 (m, 3 H), 6.67 (d, J=6.6 Hz, 2H), 6.75 (d, J=6.6 Hz, 2 H); MS (ES) m/z: 183.1 ($M^+$+H); HRMS Calcd. for $C_9H_{13}NO_3(M^+$+H): 183.0895. Found: 183.0892.

N-[2-Benzyloxy-5-(2-dibenzylamino-1-oxo-ethyl)-phenyl]-methanesulfonamide:

N-[2-Benzyloxy-5-(2-chloro-1-oxo-ethyl)-phenyl]-methanesulfonamide (EP 0 659 737) (17.0 g, 42.8 mmol) was dissolved in 200 mL of dimethylformamide and treated with dibenzylamine (22.0 g, 110 mmol). The mixture was stirred at room temperature overnight and then the solvent was removed. The residue was purified by silica gel chromatography using 20–50% ethyl acetate/hexanes as elute to give the title compound as a white solid; $^1$H NMR (300 MHz, $CDCl_3$) δ 2.94 (s, 3 H), 3.77 (s, 2 H), 3.82 (s, 2 H), 5.16 (s, 2 H), 6.75 (brs, 1 H), 6.96 (d, J=8.7 Hz, 1 H), 7.20–7.50 (m, 15 H), 7.67 (dd, J=8.7, 2.1 Hz, 1 H), 8.10 (d, J=2.1 Hz, 1 H); MS (ES) m/z: 515.2 ($M^+$+H); HRMS Calcd. for $C_{30}H_{30}N_2O_4S(M^+)$: 514.1926. Found: 514.1927.

N-[2-Benzyloxy-5-(2-dibenzylamino-1-hydroxy-ethyl)-phenyl]-methanesulfonamide:

Sodium borohydride (0.37 g, 9.7 mmol) was added in portions to a stirred solution of N-[2-benzyloxy-5-(2-dibenzylamino-1-oxo-ethyl)-phenyl]-methanesulfonamide (1.0 g, 1.9 mmol) in 20 mL of methanol/tetrahydrofuran (5:2) at room temperature and the resulting solution was stirred for 2 hours. Methylene chloride was added and the resulting solution was washed with aqueous sodium bicarbonate, dried over $MgSO_4$ and the solvent was removed. Recrystallization from methylene chloride/hexanes gave the title compound as a crystalline solid; $^1$H NMR (300 MHz, $CDCl_3$) δ 2.58 (d, J=6.7 Hz, 2 H), 2.86 (s, 2 H), 2.92 (s, 2 H), 3.55 (d, J=13.5 Hz, 2 H), 3.70 (d, J=13.5 Hz, 2 H), 4.11 (s, 1 H), 4.64 (t, J=6.7 Hz, 1 H), 5.10 (s, 2 H), 6.92 (d, J=8.5 Hz, 1 H), 7.00 (dd, J=8.5, 2.0 Hz, 1 H), 7.20–7.50 (m, 16 H), 7.89 (brs, 1 H); MS (ES) m/z: 517.1 ($M^+$+H); HRMS Calcd. for $C_{30}H_{32}N_2O_4S(M^+)$: 516.2083. Found: 516.2074.

N-[2-Benzyloxy-5-(2-amino-(1R)-1-hydroxy-ethyl)-phenyl]-methanesulfonamide:

A mixture of N-{2-benzyloxy-5-(2-iodo-(1R)-1-[(triethylsilyl)oxy]-ethyl)-phenyl}-methanesulfonamide (EP 0 659 737) (4.48 g, 8 mmol) and sodium azide (0.65 g, 10 mmol) in 100 mL of hexamethylphosphoramide was stirred at 60° C. overnight. After cooling to room temperature the mixture was diluted with diethyl ether, washed with water, dried over $Na_2SO_4$ and concentrated under reduced pressure. The residue was dissolved in 200 mL of $THF/H_2O$ (10:1) and triphenylphosphine (2.62 g, 10 mmol) was added. After overnight stirring at room temperature, the solvents were removed and the residue was partitioned between ethyl acetate and water. The organic layers were combined and dried over $MgSO_4$ and concentrated. The residue was redissolved in 100 mL of THF and tetrabutylammonium fluoride (10 mL, 1 M solution in THF) was added. The reaction was stirred for 2 hours then the solvent was removed in vacuo. The residue was purified by column chromatography on silica gel using triethylamine-methanol-methylene chloride (1:1:3) to give the title compound as a white solid; MS (ES) m/z: 337.4 ($M^+$+H).

N-[5-(2-Amino-1-hydroxy-ethyl)-2-hydroxy-phenyl]-methanesulfonamide:

To a stirred suspension of N-[2-benzyloxy-5-(2-dibenzylamino-1-hydroxy-ethyl)-phenyl]-methanesulfonamide (1.03 g, 2 mmol) and 10% Pd/C (0.4 g) in methanol (100 mL) at room temperature is added anhydrous $HCO_2NH_4$ (1.26 g, 20 mmol) under a nitrogen atmosphere. The resulting mixture is refluxed for 2 hours. After cooling to room temperature the catalyst is removed by filtration through a celite pad and washed with methanol. The filtrate is evaporated under reduced pressure to give the titled compound as a pale yellowish solid; $^1$H NMR (300 MHz, DMSO-$d_6$) δ 2.62 (dd, J=12.6, 8.7 Hz, 1 H), 2.75 (dd, J=12.6, 3.7 Hz, 1 H), 2.90 (s, 3 H), 4.47 (dd, J=8.7, 3.7Hz, 1 H), 6.84 (d, J=9.1 Hz, 1 H), 6.96 (dd, J=9.1, 2.0Hz, 1 H), 7.16 (d, J=2.1 Hz, 1 H), 8.44 (s, 1 H); MS (ES) m/z: 246.7 ($M^+$+H); HRMS Calcd. for $C_9H_{14}N_2O_4S(M^+)$: 246.0674. Found: 246.0672.

N-[5-(2-Amino-(1R)-1-hydroxy-ethyl)-2-hydroxy-phenyl]-methanesulfonamide:

Method A: A mixture of N-{2-benzyloxy-5-(2-iodo-(1R)-1-[(triethylsilyl)oxy]-ethyl)-phenyl}-methanesulfonamide (EP 0 659 737) (8.60 g, 15.3 mmol) and benzylamine (21.4 g, 200 mmol) was heated at 60° C. for 24 hours. The reaction mixture was cooled, diluted with hexanes (500 mL), and the residue was washed with diethyl ether. The combined solvents were removed and the residue was purified by silica gel column eluting with 30 to 100% $Et_2O$/hexanes. The fractions with molecular weight of 540 were concentrated and re-dissolved in 200 mL of THF and TBAF (20 mL, 1.0 M solution in THF) was added. After stirring at room temperature for 4 hours the reaction mixture was then poured into water and extracted with $CH_2Cl_2$. The organic layers were passed through a short pad of silica gel eluting with 10% methanol/$CH_2Cl_2$. The solvents were removed and the residue were dissolved in methanol (200 mL). 10% Pd/C (0.6 g) and anhydrous $HCO_2NH_4$ (6.3 g, 100 mmol) were added. The resulting mixture was refluxed under a nitrogen atmosphere for 2 hours. After cooling to room temperature the catalyst was removed by filtration through a celite pad and washed with methanol. The filtrate is evaporated under reduced pressure to give the title compound as an off-white solid; $^1$H NMR (300 MHz, MeOH-$d_4$) δ 2.95 (s, 3 H), 2.99 (dd, J=9.7, 9.2 Hz, 1 H), 3.07 (dd, J=9.7, 3.6 Hz, 1 H), 4.75 (dd, J=9.2, 3.6 Hz, 1 H), 6.90 (d, J=8.3 Hz, 1 H), 7.12 (dd, J=8.3, 2.1 Hz, 1 H), 7.38 (d, J=2.1 Hz, 1 H), 8.44 (s, 1 H); MS (ES) m/z : 246.7 ($M^+$+H) ); HRMS Calcd. for $C_9H_{14}N_2O_4S$: 246.0674. Found: 246.0672.

Method B: To a stirred solution of N-[2-benzyloxy-5-(2-Bromo-1-hydroxy-ethyl)-phenyl]-methanesulfonamide (EP 0 659 737) (15.05 g, 0.376 mol) in DMSO (150 ml) was added sodium iodide (3.76 g, 0.376 mol) and sodium azide (9.48 g, 0.150 mol). The mixture was stirred for 5 days under Nitrogen atmosphere. The reaction mixture was poured onto water and extracted three times with ethyl acetate. The combined organic layers were dried over sodium sulfate and concentrated. The residue was triturated with water and hexanes. Recovered yellow solid as of N-[5-((1R)-2-azido-1-hydroxy-ethyl)-2-benzyloxy-phenyl]-methanesulfonamide (12.85 g, 94%): $^1$H NMR (300 MHz, $CDCl_3$): δ 2.93(s, 3 H), 3.45(d, J=9.0 Hz, 2 H), 3.46(m, 1 H), 5.11(s, 2 H), 6.80(s, 1 H), 6.99(d, J=8.4 Hz, 1 H), 7.15(dd, J=6 Hz, 2.1 Hz, 1H), 7.26(s, 1 H), 7.39(s, 5 H), 7.53(d, J=2.1 Hz,1 H); MS (ES) m/z 361.4 ($M^+$–H, 70%). A mixture of N-[5-((1R)-2-Azido-1-hydroxy-ethyl)-2-benzyloxy-phenyl]-methanesulfonamide (12.85 g, 0.037 mol) and 10% Palladium on carbon (2.75 g) in ethanol (100 ml) was hydrogenated under 45 PSI for two days. The reaction mixture was filtered through celite and concentrated. The title compound was recovered as a tan solid (6.08 g, 66%): $^1$H NMR (300 MHz, DMSO-$d_6$): δ 2.60(m, 2 H), 2.87(s, 3 H), 4.34(m, 1 H), 6.79(d, J=9.0 Hz, 1 H), 6.89(d, J=9.0 Hz, 2 H).

The following procedures describe the preparation of intermediates useful in the preparation of compounds of this invention.

INTERMEDIATE 1

(2S)-1-(1-Benzhydryl-azetidin-3-ylideneamino)-3-(4-benzyloxy-phenoxy)-propan-2-ol A mixture of (2S)1-Amino-3-(4-benzyloxy-phenoxy)-propan-2-ol (1.64 g, 6 mmol) and 1-(diphenylmethyl)-3-azetidinone (1.19 g, 5 mmol) in methanol (20 ml) was treated with trimethylorthoformate (1.59 g, 15 mmol), and stirred at room temperature for 2 days. The resulting suspension was filtered, and the precipitate washed with 3×5 ml of methanol, and dried in vacuo to give 1.96 g of a white solid. The methanol filtrate was evaporated, and the residue was dissolved in ethyl acetate. The ethyl acetate solution was filtered through a pad of silica gel, and eluted with 2×30 ml of ethyl acetate. The combined filtrate was evaporated, and the residue triturated with a mixture of ether and hexanes to give an additional 0.30 g of product; m.p. 141–142° C.; MS (ES) m/z 748 ($MH^+$); HRMS (El) Calcd. for $C_{32}H_{32}N_2O_3$ ($M^+$): 492.2413, Found: 492.2397.

INTERMEDIATE 2

(2S)-1-(1-Benzhydryl-azetidin-3-ylamino)-3-(4-benzyloxy-phenoxy)-propan-2-ol

To a solution of (2S)-1-(1-Benzhydryl-azetidin-3-ylideneamino)-3-(4-benzyloxy-phenoxy)-propan-2-ol (0.49 g, 1 mmol) in tetrahydrofuran (4 ml) was added 1.2 ml of borane-tetrahydrofuran (1.0 M in THF), and the mixture was stirred at room temperature for 20 h. It was then quenched with 1.5 ml of 2 N NaOH, and the volatiles were evaporated. The aqueous solution was removed, and the residue was washed with water, and treated with 3 ml of 2 N HCL and 3 ml of methanol for 20 h. The mixture was then made alkaline with 1 N NaOH, and the methanol was evaporated. The resulting suspension was filtered, and the precipitate washed with water, and dried in vacuo to give 0.46 g of a white solid; m.p. 109–110°C.; MS (ES) m/z 495.7 ($MH^+$); HRMS (El) Calcd. for $C_{32}H_{34}N_2O_3$ ($M^+$): 494.2570, Found: 494.2561.

INTERMEDIATE 3

(1-Benzhydryl-azetidin-3-yl)-[(2S)-3-(4-benzyloxy-phenoxy)-2-hydroxy-propyl]-carbamic acid tert-butyl ester To a solution of (2S)-1-(1-Benzhydryl-azetidin-3-ylamino)-3-(4-benzyloxy-phenoxy)-propan-2-ol (0.49 g, 1 mmol) in dichloromethane (5 ml) was added di-tert-butyldicarbonate (0.26 g, 1.2 mmol), and the mixture was stirred at room temperature for 2 h. The solvent was then evaporated, and the residue was dissolved in hexanes. The solution was passed through a pad of silica gel, first eluting with hexanes, and then with a mixture of ethyl acetate-hexanes (2:1). The latter eluent was evaporated to give 0.59 g of a white solid; m.p. 95–96 ° C.; MS (ES) m/z 595.3 ($MH^+$); HRMS (Cl) Calcd. for $C_{37}H_{43}N_2O_5$ ($MH^+$): 595.3172, Found: 595.3181.

INTERMEDIATE 4

Azetidin-3-yl-[(2S)-2-hydroxy-3-(4-hydroxyphenoxy)-propyl]-carbamicacid tert-butyl ester To a solution of (1-Benzhydryl-azetidin-3-yl)-[(2S)-3-(4-benzyloxy-phenoxy)-2-hydroxy-propyl]-carbamic acid tert-butyl ester (0.55 g, 0.9 mmol) in methanol (20 ml) was added ammonium formate (2.0 g, 30 mmol), and 0.2 g of 10% Pd/C. The mixture was stirred at reflux for 18 h. After cooling to room temperature, it was filtered through Celite. The solvent was evaporated to give 0.31 g of a beige solid; m.p. 130–134° C.; MS (ES) m/z 339.1 (MH$^+$); HRMS (EI) Calcd. for $C_{37}H_{42}N_2O_5$ (M$^+$): 338.1841, Found: 338.1833.

INTERMEDIATE 5

[1-(4-Butoxy-benzenesulfonyl)-azetidin-3-yl]-[(2S)-2-hydroxy-3-(4-hydroxy-phen oxy)-propyl]-carbamic acid tert-butyl ester

INTERMEDIATE 6

4-Butoxy-benzenesulfonic acid 4-(3-{[1-(4-butoxy-benzenesulfonyl)-azetidin-3-yl]-tert-butoxycarbonyl-amino}-2-hydroxy-propoxy)-phenylester To a solution of Azetidin-3-yl-[(2S)-2-hydroxy-3-(4-hydroxy-phenoxy)-propyl]-carbamicacid tert-butyl ester (0.28 g, 0.8 mmol) in chloroform (4 ml) was added triethylamine (0.2 g, 2 mmol), and 4-butoxybenzenesulfonyl chloride (0.26 g, 1.0 mmol). The mixture was stirred at reflux for 5 h, and then quenched with 50% sodium bicarbonate solution. The chloroform was evaporated and the aqueous solution was removed. The residue was chromatographed (silica gel, ethyl acetate-hexanes/2:1) to give: (1) 0.13 g of [1-(4-Butoxy-benzenesulfonyl)-azetidin-3-yl]-[(2S)-2-hydroxy-3-(4-hydroxy-phenoxy)-propyl]-carbamic acid tert-butyl ester as a colorless foam; MS (ES) m/z 551.1 (MH$^+$); HRMS (EI) Calcd. for $C_{27}H_{38}N_2O_8S$ (M$^+$): 550.2349, Found: 550.2353, and (2) 0.17 g of 4-Butoxy-benzenesulfonic acid 4-(3-{[(1-(4-butoxy-benzenesulfonyl)-azetidin-3-yl]-tert-butoxycarbonyl-amino}-2-hydroxy-propoxy)-phenylester as a colorless foam; MS (ES) m/z 763.3 (MH$^+$); HRMS (ES) Calcd. for $C_{37}H_{51}N_2O_{11}S_2$ (MH$^+$): 763.2934, Found: 763.2899.

INTERMEDIATE 7

4-Butoxy-benzenesulfonic acid 1-(4-butoxy-benzenesulfonyl)-azetidin-3-yl ester

To a solution of 3-hydroxyazetidine (0.41 g, 4 mmol) in dichloromethane (8 ml) was added triethylamine (0.51 g, 5 mmol) followed by 4-butoxybenzenesulfonyl chloride (1.08 g, 4.2 mmol). The mixture was stirred at room temperature for 24 h when a catalytic amount of 4-dimethylaminopyridine and additional triethylamine (0.51 g, 5 mmol) and 4-butoxybenzenesulfonyl chloride (1.08 g, 4.2 mmol) were added. Stirring was continued for 2 days. The volatiles were then evaporated, and the residue was treated with hexanes and water. The resulting suspension was filtered, and the precipitate washed with 10% sodium carbonate solution, water, and hexanes, and then dried in vacuo to give 1.75 g of an off-white solid; m.p. 90–93 ° C.; MS (ES) m/z 498.0 (MH$^+$); HRMS (EI) Calcd. for $C_{23}H_{31}NO_7S_2$ (M$^+$): 497.1542, Found: 497.1536.

INTERMEDIATE 8

Benzyl-[1-(4-butoxy-benzenesulfonyl)-azetidin-3-yl]-amine

To a solution of 4-Butoxy-benzenesulfonic acid 1-(4-butoxy-benzenesulfonyl)-azetidin-3-yl ester (0.99 g, 2 mmol) in tetrahydrofuran (4 ml) was added benzylamine (0.86 g, 8 mmol) and the mixture was stirred at 100° C. for 5 days. It was then washed with hexanes, and the residue was extracted with ether. The ether solution was evaporated, and the residue was chromatographed (silica gel, ethyl acetate-hexanes/1:1)to give 0.40 g of an amber gum; MS (ES) m/z 375.0 (MH$^+$); HRMS (ES) Calcd. for $C_{20}H_{27}N_2O_3S$ (MH$^+$): 375.1742, Found: 375.1743.

INTERMEDIATE 9

1-{Benzyl-[1-(4-butoxy-benzenesulfonyl)-azetidin-3-yl]-amino}-3-(9H-carbazol-4-yloxy)-propan-2-ol To a solution of benzyl-[1-(4-butoxy-benzenesulfonyl)-azetidin-3-yl]-amine (0.14 g, 0.37 mmol) in methanol (2 ml) was added (2S)-3-(9H-carbazol-4-yloxy)-methyl oxirane (0.11 g, 0.45 mmol) and the mixture was stirred at reflux for 3 days. The methanol was then evaporated, and the residue was washed with a mixture of ether and hexanes to give 0.24 g of an off-white solid; m.p. 65–67° C.; MS (ES) m/z 614.2 (MH$^+$); HRMS (ES) Calcd. for $C_{35}H_{40}N_3O_5S$ (MH$^+$): 614.2689, Found: 614.2706.

INTERMEDIATE 10

Methanesulfonic acid 1-benzhydrylazetidin-3-yl ester

To a solution of 1-benzhydryl-3-hydroxyazetidine (4.78 g, 20 mmol) in dichloromethane (35 ml) was added triethylamine (2.43 g, 24 mmol) and cooled to 0° C. A solution of methanesulfonyl chloride (1.86 ml, 24 mmol) in dichloromethane (5 ml) was then introduced slowly, and the resulting suspension was stirred at room temperature for 18 h. The volatiles were evaporated, and the residue was extracted with a mixture of ether and ethyl acetate. The combined extract was filtered through Magnosol and the filtrate evaporated to give 6.01 g of a light yellow solid; MS (ES) m/z 318.0 (MH$^+$).

INTERMEDIATE 11

(1-Benzhydryl-azetidin-3-yl)-benzyl-amine

To a solution of methanesulfonic acid 1-benzhydrylazetidin-3-yl ester (0.32 g, 1 mmol) in N,N'-dimethylpropyleneurea (0.5 ml) was added benzylamine (0.5 ml, 5 mmol), and the mixture was stirred at 70° C. for 18 h. It was then cooled to room temperature and diluted with ether (30 ml). The resulting suspension was filtered and the ether solution was evaporated. The residue was partitioned between hexanes and water, and hexanes solution was washed with saturated sodium bicarbonate solution and dried over anhydrous sodium sulfate. It was then filtered through a pad of silica gel, and the filter pad was eluted with a 1:1 mixture of ether-hexanes. Evaporation of solvents followed by trituration with isooctane gave 0.22 g of a white solid; m.p. 73–75° C.; MS (ES) m/z 329.0 (MH$^+$); HRMS (EI) Calcd. for $C_{23}H_{24}N_2$ (M$^+$): 328.1940, Found: 328.1936.

INTERMEDIATE 12

(1-Benzhydryl-azetidin-3-yl)-benzyl-carbamic acid tert-butyl ester

To a solution of (1-benzhydryl-azetidin-3-yl)-benzyl-amine (0.41 g, 1.2 mmol) in dichloromethane (5 ml) was added di-tert-butyldicarbonate (0.31 g, 1.4 mmol), and the mixture was stirred at room temperature for 3 h. It was then stirred with 5 ml of 10% sodium carbonate solution for 1 h. The mixture was extracted with 20 ml of ethyl acetate, and the organic solution was washed with 1 N NaOH and brine, dried over anhydrous sodium sulfate, and evaporated. The residue was washed with hexanes to give 0.49 g of a white solid; m.p. 117–118° C.; MS (ES) m/z 429.1 (MH$^+$); HRMS (FAB) Calcd. for $C_{28}H_{33}N_2O_2$ (MH$^+$): 429.2542, Found: 429.2542.

INTERMEDIATE 13

Azetidin-3-yl-benzyl-carbamic acid tert-butyl ester

To a solution of (1-Benzhydryl-azetidin-3-yl)-benzyl-carbamic acid tert-butyl ester (0.43 g, 1 mmol) in a mixture of methanol (18 ml) and dichloromethane (2 ml) was added ammonium formate (1.3 g, 20 mmol), and 0.15 g of 10% Pd/C. The mixture was stirred at reflux for 18 h. After cooling to room temperature, it was filtered through Celite. The solvents were evaporated, and the residue was washed with hexanes and then extracted with dichloromethane. The dichloromethane solution was evaporated to give 0.24 g of a white solid; m.p. 144–145° C.; MS (ES) m/z 263.0 (MH$^+$).

INTERMEDIATE 14

Benzyl-[1-(4-fluoro-benzenesulfonyl)-azetidin-3-yl]-carbamic acid tert-butyl ester To a solution of azetidin-3-yl-benzyl-carbamic acid tert-butyl ester (0.20 g, 0.76 mmol) in dichloromethane (2 ml) was added triethylamine (0.15 g, 1.5 mmol) followed by 4-fluorobenzenesulfonyl chloride (0.17 g, 0.84 mmol). The mixture was stirred at room temperature for 18 h. It was then quenched with 50% sodium carbonate solution and the volatiles were evaporated. The residue was diluted with ethyl acetate, washed with brine, dried over anhydrous sodium sulfate, and evaporated. The crude material was washed with hexanes to give 0.29 g of a colorless gum; MS (ES) m/z 420.9 (MH$^+$); HRMS (FAB) Calcd. for $C_{21}H_{26}FN_2O_4S$ (MH$^+$): 421.1597, Found: 421.1633.

INTERMEDIATE 15

Benzyl-[1-(4-butylamino-benzenesulfonyl)-azetidin-3-yl]-carbamicacid tert-butyl ester To a solution of Benzyl-[1-(4-fluoro-benzenesulfonyl)-azetidin-3-yl]-carbamicacid tert-butyl ester (0.21 g, 0.5 mmol) in N,N'-dimethylpropyleneurea (0.5 ml) was added butylamine (0.15 g, 2 mmol) and potassium carbonate (0.07 g, 0.5 mmol), and the mixture was stirred at 50° C. for 2 days. It was then cooled to room temperature and diluted with water (20 ml). The aqueous phase was removed, and the residue dissolved in ether (20 ml). The ether solution was washed with 0.5 N HCl, saturated sodium bicarbonate solution, and brine, and dried over anhydrous sodium sulfate. It was then filtered through a pad of silica gel. The filtrate was evaporated, and the residue was triturated with hexanes to give 0.23 g of a white solid; m.p. 115–116° C.; MS (ES) m/z 474.1 (MH$^+$); HRMS (EI) Calcd. for $C_{25}H_{35}N_3O_4S$ (M$^+$): 473.2348, Found: 473.2338.

INTERMEDIATE 16

Benzyl-[1-(4-butylamino-benzenesulfonyl)-azetidin-3-yl]-amine

To a solution of Benzyl-[1-(4-butylamino-benzenesulfonyl)-azetidin-3-yl]-carbamicacid tert-butyl ester (0.19 g, 0.4 mmol) in dichloromethane (4 ml) was added trifluoroacetic acid (0.31 ml, 4 mmol). The mixture was stirred at room temperature for 2 h, and then quenched with saturated sodium carbonate solution, and extracted with dichloromethane. The organic solution was washed with brine, dried over sodium sufate, and evaporated. The crude product was chromatographed on silica gel (ethyl acetate-hexanes/3:2) to give 0.09 g of a colorless foam; MS (ES) m/z 374.1 (MH$^+$); HRMS (EI) Calcd. for $C_{20}H_{27}N_3O_2S$ (M$^+$): 373.1824, Found: 373.1822.

INTERMEDIATE 17

1-{Benzyl-[1-(4-butylamino-benzenesulfonyl)-azetidin-3-yl]-amino}-3-(4-benzyloxy-phenoxy)-propan-2-ol To a solution of benzyl-[1-(4- butylamino-benzenesulfonyl)-azetidin-3-yl]-amine (65 mg, 0.17 mmol) in methanol (2 ml) was added (2S)-4-(benzyloxy-phenoxy)-methyl oxirane (0.11 g, 0.42 mmol), and the mixture was stirred at reflux for 3 days. The methanol was then evaporated, and the residue was washed with a mixture of ether and hexanes to give 0.11 g of a colorless gum; MS (ES) m/z 630.2 (MH$^+$); HRMS (FAB) Calcd. for $C_{36}H_{44}N_3O_5S$ (MH$^+$): 630.3002, Found: 630.3008.

INTERMEDIATE 18

{[4-(3-{Benzyl-[3-(4-benzyloxy-phenoxy)-2-hydroxy-propyl]-amino}-azetidine-1-sulfonyl)-phenyl]-butyl-amino}-acetic acid methyl ester To a solution of 1-{benzyl-[1-(4-butylamino-benzenesulfonyl)-azetidin-3-yl]amino}-3-(4-benzyloxy-phenoxy)-propan-2-ol (0.10 g, 0.15 mmol) in N,N'-dimethylpropyleneurea (1 ml) was added methyl bromoacetate (46 mg, 0.3 mmol) and potassium carbonate (28 mg, 0.2 mmol), and the mixture was stirred at 50° C. for 2 days. It was then cooled to room temperature and diluted with water (20 ml). The aqueous phase was removed, and the residue dissolved in ethyl acetate (20 ml). The organic solution was washed with brine, and dried over anhydrous sodium sulfate. It was then filtered and evaporated, and the residue was chromatographed on silica gel (ethyl acetate-hexanes/1:1) to give 50 mg of a colorless gum; MS (ES) m/z 702.2 (MH$^+$); HRMS (FAB) Calcd. for $C_{39}H_{48}N_3O_7S$ (MH$^+$): 702.3213, Found: 702.3231.

INTERMEDIATE 19

N-[5-((1R)-2-Benzylamino-1-triethylsilanyloxy-ethyl)-2-benzyloxy-phenyl]-methanesulfonamide N-[2-benzyloxy-5-((1R)-2-iodo-1-triethylsilanyloxy-ethyl)-phenyl]-methanesulfonamide (0.56 g, 1 mmol) was dissolved in benzylamine (0.54 g, 5 mmol) and stirred at 65° C. for 22 h.

The mixture was then cooled to room temperature, and stirred with hexanes. The hexanes solution was filtered through a pad of silica gel, and the residue was stirred with ether (10 ml). The ether solution was diluted with 10 ml of hexanes, and passed through the silica gel pad. The filter pad was eluted with ether-hexanes (1:1 to 3:1), and the filtrate was evaporated. The residue was washed with isooctane to give 0.44 g of a colorless gum; MS (ES) m/z 541.1 (MH$^+$); HRMS (EI) Calcd. for $C_{29}H_{40}N_2O_4SSi$ (M$^+$): 540.2478, Found: 540.2472.

INTERMEDIATE 20

3-Oxo-azetidine-1-carboxylic acid 1-chloro-ethyl ester

To a solution of 1-(diphenylmethyl)-3-azetidinone (0.24 g, 1 mmol) in dichloromethane (2 ml) was added 1-choloroethyl chloroformate (0.13 ml, 1.2 mmol) at 0° C. After 0.5 h, the mixture was warmed to room temperature for 2 h. 1,8-Bis-(dimethylamino)-naphthalene (43 mg, 0.2 mmol) was then added, and stirring was continued for 18 h. The solvent was evaporated and the residue was extracted with ethyl acetate. The ethyl acetate solution was filtered through silica gel and the filtrate evaporated. The residue was triturated with hexanes to give 0.14 g of an off-white solid; $^1$H NMR (CDCl$_3$) δ 1.83 (d, 3H), 4.84 (s, 4H), 6.54–6.60 (q,1 H).

INTERMEDIATE 21

N-[5-((1R)-2-{Benzyl-[1-(4-butoxy-benzenesulfonyl)-azetidin-3-yl]-amino}-1-triethylsilanyloxy-ethyl)-2-benzyloxy-phenyl]-methanesulfonamide

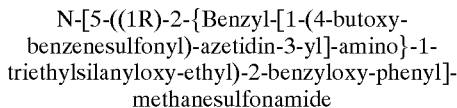

To a mixture of 3-oxo-azetidine-1-carboxylic acid 1-chloro-ethyl ester (0.09 g, 0.5 mmol) and N-[5-((1R)-2-Benzylamino-1-triethylsilanyloxy-ethyl)-2-benzyloxy-phenyl]-methanesulfonamide (0.32 g, 0.6 mmol) in 1,2-dichloroethane (2 ml) was added sodium triacetoxyborohydride (0.16 g, 0.7 mmol). The mixture was stirred at room temperature for 18 h, and then quenched with 10 ml of water and 5 ml of saturated sodium bicarbonate solution. Extraction with dichloromethane (20 ml) and evaporation of solvents gave 0.43 g of an amber gum which was dissolved in methanol and refluxed for 18 h. The methanol was evaporated and the residue was washed with ether-hexanes to give 0.17 g of a beige foam. 0.12 g of this material was dissolved in dichloromethane (2 ml) and treated with triethylamine (41 mg, 0.4 mmol) and 4-butoxybezenesulfonyl chloride (77 mg, 0.3 mmol). The mixture was stirred at room temperature for 2 h, and then quenched with saturated sodium bicarbonate solution. The aqueous was extracted with ethyl acetate, and the organic solution was dried over anhydrous sodium sulfate and evaporated. The crude material was chromatographed on silica gel (ethyl acetate-hexanes/1:3) to give 0.12 g of a colorless gum; MS (ES) m/z 808.1 (MH$^+$); HRMS (FAB) Calcd. for C$_{42}$H$_{58}$N$_3$O$_7$S$_2$Si (MH$^+$): 808.3486, Found: 808.3451.

INTERMEDIATE 22

1-(4-Butoxy-benzenesulfonyl)-pyrrolidin-3-ol

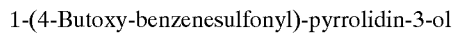

To a solution of DL-3-pyrrolidinol (0.87 g, 10 mmol) in dichloromethane (10 ml) was added triethylamine (1.21 g, 12 mmol) and 4-butoxybezenesulfonyl chloride (2.69 g, 10.5 mmol). The mixture was stirred at room temperature for 2 h. It was then treated with 10 ml of saturated sodium carbonate solution for 18 h. The mixture was diluted with water, and the organic solvents were evaporated. The resulting suspension was filtered, and the precipitate was washed with water and hexanes, and dried to give 2.89 g of an off-white solid; m.p. 83–84° C.; MS (ES) m/z 299.9 (MH$^+$); HRMS (Cl) Calcd. for C$_{14}$H$_{22}$NO$_4$S (MH$^+$): 300.1269, Found: 300.1272.

INTERMEDIATE 23

Methanesulfonic acid 1-(4-butoxy-benzenesulfonyl)-pyrrolidin-3-yl ester

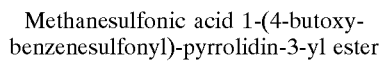

To a solution of 1-(4-Butoxy-benzenesulfonyl)-pyrrolidin-3-ol (1.50 g, 5 mmol) in dichloromethane (8 ml) was added triethylamine (0.61 g, 6 mmol) and cooled to 0° C. A solution of methanesulfonyl chloride (0.46 ml, 6 mmol) in dichloromethane (2 ml) was then introduced slowly, and the resulting suspension was stirred at 0° C. for 15 min., and at room temperature for 2 h. The solvent was evaporated, and the residue was stirred with 10 ml of water, 5 ml of saturated sodium carbonate solution, and 20 ml of hexanes. The resulting suspension was filtered, and the precipitate was washed with water and hexanes, and dried to give 1.88 g of a white solid; m.p. 80–81° C.; MS (ES) m/z 377.9 (MH$^+$); HRMS (El) Calcd. for C$_{15}$H$_{23}$NO$_6$S$_2$ (M$^+$): 377.0967, Found: 377.0969.

INTERMEDIATE 24

Benzyl-[1-(4-butoxy-benzenesulfonyl)-pyrrolidin-3-yl]-amine

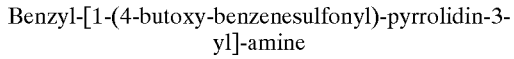

A solution of methanesulfonic acid 1-(4-butoxy-benzenesulfonyl)-pyrrolidin-3-yl ester (1.51 g, 4 mmol) in tetrahydrofuran (8 ml) was added benzylamine (3.46 g, 32 mmol) and the mixture was stirred at 100° C. for 2 days. After cooling to room temperature the tetrahydrofuran was evaporated, and the residue washed with hexanes. The solid was stirred with 10% sodium carbonate solution (30 ml) and ethyl acetate (40 ml), and the organic solution was washed brine, dried over anhydrous sodium sulfate, and filtered through Magnolsol. The filtrate was evaporated, and the residue was washed with hexanes to give 1.49 g of a white solid; m.p. 99–100° C.; MS (ES) m/z 389.0 (MH$^+$); HRMS (El) Calcd. for C$_{21}$H$_{28}$N$_2$O$_3$S (M$^+$): 388.1820, Found: 388.1826.

INTERMEDIATE 25

1-{Benzyl-[1-(4-butoxy-benzenesulfonyl)-pyrrolidin-3-yl]-amino}-3-(9H-carbazol-4-yloxy)-propan-2-ol

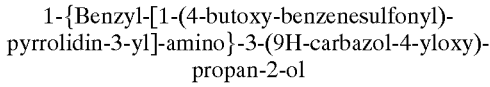

To a solution of benzyl-[1-(4-butoxy-benzenesulfonyl)-pyrrolidin-3-yl]-amine (0.16 g, 0.4 mmol) in methanol (2 ml) was added (2S)-3-(9H-carbazol-4-yloxy)-methyl oxirane (0.12 g, 0.5 mmol) and the mixture was stirred at reflux for 3 days. The methanol was then evaporated, and the residue was washed with a mixture of ether and hexanes to give 0.28 g of an off-white solid; m.p. 73–76° C.; MS (ES) m/z 628.2 (MH$^+$); HRMS (El) Calcd. for C$_{36}$H$_{41}$N$_3$O$_5$S (M$^+$): 627.2767, Found: 627.2808.

INTERMEDIATE 26

5-[4-(4-Oxo-piperidine-1-sulfonyl)-benzyl]-thiazolidine-2,4-dione

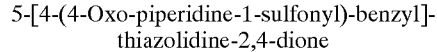

The title compound was prepared from 4-(2,4-dioxo-thiazolidin-5-ylmethyl)-benzene-sulfonylchloride (J. Med. Chem. 1992, 35, 1853) and 4-piperidone monohydrate hydrochloride according to the procedure of Intermediate 22 as a white solid; 1H NMR (300 MHz, DMSO-d6) □ 2.40–2.50 (m, 4 H), 3.20–3.40 (m, 5 H), 3.50 (dd, J=14.1, 4.7 Hz, 1 H), 5.00 (dd, J=10.4, 4.7 Hz, 1 H), 7.56 (d, J=8.4 Hz, 2 H), 7.76 (d, J=8.4 Hz, 2 H), 12.09 (s, 1 H); MS (ES) m/z: 368.9 (M++H); HRMS Calcd. for C15H16N2O5S2 (M++H): 368.0501. Found: 368.0481. Anal. Calcd. for C15H16N2O5S2: C, 48.90; H, 4.38; N, 7.60. Found: C,48.63; H, 4.35; N, 7.38.

INTERMEDIATE 27

1-(4-Butoxy-benzenesulfonyl)-piperidin-4-one

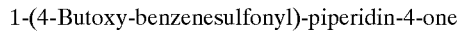

The title compound was prepared from 4-butoxybezenesulfonyl chloride and 4-piperidone monohydrate hydrochloride according to the procedure of Intermediate 22 as an off-white solid; $^1$H NMR (CDCl$_3$) δ 0.98 (t, J=7.38 Hz, 3H), 1.44–1.54 (m, 4H), 1.75–1.84 (m, 4H), 2.54 (t, J=6.24 Hz, 2H), 3.37 (t, J=6.18 Hz, 2H), 4.02 (t, J=6.48 Hz, 2H), 6.99 (dt, J=2.91 Hz, 4.77 Hz, 2H), 7.72(dt, J=2.91 Hz, 4.86 Hz, 2H); MS (ES) m/z 311.9 (MH$^+$); HRMS for C$_{15}$H$_{21}$NO$_4$S: 311.1196; Anal. Calcd. for C$_{15}$H$_{21}$NO$_4$S: C, 57.86; H, 6.80; N, 4.50. Found: C, 57.69; H, 6.50; N, 4.25.

INTERMEDIATE 28

1-(Benzo[1,2,5]thiadiazole-4-sulfonyl)-piperidin-4-one

The title compound was prepared from benzo[1,2,5]thiadiazole-4-sulfonyl chloride and 4-piperidone monohydrate hydrochloride according to the procedure of Intermediate 22 as an off-white solid; $^1$H NMR (CDCl$_3$) δ 2.57 (t, J=6.21 Hz, 2H), 3.77 (t, J=6.21 Hz, 2H), 7.60–7.84 (m, 1H), 8.25–8.32 (m, 1H), 8.40–8.46 (m, 1H); MS (ES) m/z 297.9 (MH$^+$). C$_{11}$H$_{11}$N$_3$O$_3$S$_2$

INTERMEDIATE 29

1-(4-Methoxy-benzenesulfonyl)-piperidin-4-one

The title compound was prepared from 4-methoxybezenesulfonyl chloride and 4-piperidone monohydrate hydrochloride according to the procedure of Intermediate 22 as an off-white solid; $^1$H NMR (CDCl$_3$) δ 2.54 (t, J=4.80 Hz, 4H), 3.37 (t, J=4.80 Hz, 4H), 3.88 (s, 3H), 7.01 (dt, J=1.50 Hz, 3.90 Hz, 2H), 7.73 (dt, J=1.50 Hz, 3.60 Hz, 2H); MS (ES) m/z 269.8 (MH$^+$); HRMS for C$_{12}$H$_{15}$NO$_4$S: 269.0722; Anal. Calcd. for C$_{12}$H$_{15}$NO$_4$S: C, 53.52; H, 5.61; N, 5.20. Found: C, 53.35; H, 5.60; N, 5.15.

INTERMEDIATE 30

1-(3,4-Dimethoxy-benzenesulfonyl)-piperidin-4-one

The title compound was prepared from 3,4-dimethoxybezenesulfonyl chloride and 4-piperidone monohydrate hydrochloride according to the procedure of Intemediate 22 as a white solid; $^1$H NMR (CDCl$_3$) δ 2.55 (t, J=6.15 Hz, 4H), 3.40 (t, J=6.15 Hz, 4H), 3.93 (s, 3H), 3.95 (s, 3H), 6.97 (d, J=8.46 Hz, 1H), 7.23 (d, J=2.04 Hz, 1H), 7.41 (dd, J=2.10 Hz, 8.49 Hz, 1H); MS (ES) m/z 299.9 (MH$^+$); HRMS for C$_{13}$H$_{17}$NO$_5$S: 299.0834; Anal. Calcd. for C$_{13}$H$_{17}$NO$_5$S: C, 52.16; H, 5.72; N, 4.68. Found: C, 52.13; H, 5.80; N, 4.59.

INTERMEDIATE 31

1-(Dibenzofuran-2-sulfonyl)-piperidin-4-one

To a mixture of 4-piperidone hydrochloride monohydrate (0.95 g, 0.62 mmol) and dibenzofuran sulfonyl chloride (0.15 g, 0.56 mmol) in 5 ml anhydrous methylene chloride was added triethylamine (0.24 mL, 1.69 mmol), which was stirred overnight. The reaction mixture was quenched with water and the solvent was removed in vacuo. The residue was then extracted twice with ethyl acetate. The organic layer was then washed twice with water, twice with brine, dried over sodium sulfate and then concentrated in vacuo. The resulting solid was then triturated with hexanes, giving a white solid; $^1$H NMR (CDCl$_3$) δ 2.58 (t, J=6.18 Hz, 4H), 3.46 (t, J=6.18 Hz, 4H), 7.33–7.47 (m, 1H), 7.54–7.60 (m, 1H), 7.64 (d, J=7.53 Hz, 1H), 7.72 (d, J=8.67 Hz, 1 H), 7.90 (dd, J=1.95 Hz, 1.95 Hz, 1 H), 8.02 (d, J=7.86 Hz, 1 H), 8.46 (d, J=1.77 Hz, 1 H); MS (ES) m/z 330.0 (MH$^+$); HRMS for C$_{17}$H$_{15}$NO$_4$S: 329.0709.

INTERMEDIATE 32

1-Hexyl-3-[4-(4-oxo-piperidine-1-sulfonyl)-phenyl]-urea

The title compound was prepared from 1-hexyl-urea-4-benzenesulfonyl chloride and 4-piperidone monohydrate hydrochloride according to the procedure of Intermediate 31 as a translucent solid; $^1$H NMR (CDCl$_3$) δ 0.86–0.95 (m, 3H), 1.29–1.38 (m, 6H), 1.48–1.55 (m, 2H), 2.54 (t, J=6.12 Hz, 4H), 3.22–3.28 (m, 2H), 3.36 (t, J=6.15 Hz, 4H), 5.07 (t, J=5.55 Hz, 1H), 7.04 (s, 1H), 7.50 (d, J=8.82 Hz, 2H), 7.65 (d, J=8.79 Hz, 2H); MS (ES) m/z 382.0 (MH$^+$); HRMS for C$_{18}$H$_{27}$N$_3$O$_4$S: 381.1704.

The following procedures describe the preparation of representative examples of this invention.

EXAMPLE 1

4-{(2S)-3-[1-(4-Butoxy-benzenesulfonyl)-azetidin-3-ylamino]-2-hydroxy-propoxy}-phenol To a solution of [1-(4-butoxy-benzenesulfonyl)-azetidin-3-yl]-[(2S)-2-hydroxy-3-(4-hydroxy-phenoxy)-propyl]-carbamic acid tert-butyl ester (0.11 g, 0.2 mmol) in dichloromethane (2 ml) was added trifluoroacetic acid (0.15 ml, 2 mmol). The mixture was stirred at room temperature for 2 h, and then quenched with saturated sodium carbonate solution and extracted with dichloromethane. The organic solution was washed with brine, dried over sodium sufate, and evaporated to give 0.10 g of a white solid; m.p. 55–58° C.; MS (ES) m/z 451 (MH$^+$); HRMS (Cl) Calcd. for C$_{22}$H$_{31}$N$_2$O$_6$S (MH$^+$): 451.1903, Found: 451.1882.

EXAMPLE 2

4-Butoxy-benzenesulfonic acid 4-{3-[1-(4-butoxy-benzenesulfonyl)-azetidin-3-ylamino]-2-hydroxy-propoxy}-phenyl ester To a solution of 4-butoxy-benzenesulfonic acid 4-(3-{[1-(4-butoxybenzene-sulfonyl)azetidin-3-yl]-tert-butoxycarbonyl-amino}-2-hydroxy-propoxy)-phenylester (0.12 g, 0.15 mmol) in dichloromethane (2 ml) was added trifluoroacetic acid (0.12 ml, 1.5 mmol). The mixture was stirred at room temperature for 4 h, and then quenched with saturated sodium carbonate solution and extracted with dichloromethane. The organic solution was washed with brine, dried over sodium sufate, and evaporated to give 0.10 g of a white solid; MS (ES) m/z 663.1 (MH$^+$); HRMS (ES) Calcd. for C$_{32}$H$_{43}$N$_2$O$_9$S$_2$ (MH$^+$): 663.2410, Found: 663.2401.

EXAMPLE 3

1-[1-(4-Butoxy-benzenesulfonyl)-azetidin-3-ylamino]-3-(9H-carbazol-4-yloxy)-propan-2-ol To a solution of 1-{Benzyl-[1-(4-butoxy-benzenesulfonyl)-azetidin-3-yl]-amino}-3-(9H-carbazol-4-yloxy)-propan-2-ol (0.18 g, 0.3 mmol) in methanol (6 ml) was added ammonium formate (0.29 g, 4.5 mmol), and 0.045 g of 10% Pd/C. The mixture was stirred at reflux for 18 h. After cooling to room temperature, it was filtered through Celite. The solvent was evaporated and the residue triturated with isopropyl ether to give 0.14 g of a white solid; m.p. 81–84° C.; MS (ES) m/z 524.0 (MH$^+$); HRMS (ES) Calcd. for C$_{28}$H$_{34}$N$_3$O$_5$S (MH$^+$): 524.2219, Found: 524.2252.

EXAMPLE 4

[Butyl-(4-{3-[2-hydroxy-3-(4-hydroxy-phenoxy)-propylamino]-azetidine-1-sulfonyl}-phenyl)-amino]-acetic acid methyl ester To a solution of {[4-(3-{Benzyl-[3-(4-benzyloxy-phenoxy)-2-hydroxy-propyl]-amino}-azetidine-1-sulfonyl)- phenyl]-butyl-amino}-acetic acid methyl ester (35 mg, 0.05 mmol) in methanol (2 ml) was added ammonium formate (49 mg, 0.75 mmol), and 8 mg of 10% Pd/C. The mixture was stirred at reflux for 18 h. After cooling to room temperature, it was filtered through Celite. The solvent was evaporated and the residue triturated with ether-hexanes to give 30 mg of an off-white foam; MS (ES) m/z 522.0 (MH$^+$); HRMS (FAB) Calcd. for $C_{25}H_{36}N_3O_7S$ (MH$^+$): 522.2274, Found: 522.2293.

EXAMPLE 5

N-(5-{2-[1-(4-Butoxy-benzenesulfonyl)-azetidin-3-ylamino]-1-hydroxy-ethyl}-2-hydroxy-phenyl)-methanesulfonamide To a solution of N-[5-((1R)-2-{benzyl-[1-(4-butoxy-benzenesulfonyl)-azetidin-3-yl]-amino}-1-triethylsilanyloxy-ethyl)-2-benzyloxy-phenyl]-methanesulfonamide (0.10 g, 0.12 mmol) in tetrahydrofuran (1 ml) was added 0.2 ml of tetrabutylammonium fluoride (1 M in THF). After 2 h at room temperature, the mixture was treated with water and extracted with ethyl acetate. The organic solution was dried over anhydrous sodium sulfate, and evaporated. The residue obtained was dissolved in methanol (3 ml), and treated with ammonium formate (0.12 g, 1.8 mmol) and 10% Pd/C (20 mg) at reflux for 18 h. It was then cooled to room temperature, filtered through Celite, and eluted with more methanol. The filtrate was evaporated, and the residue washed with ether-hexanes to give 55 mg of an off-white solid; m.p. 67–70° C.; MS (ES) m/z 514.0 (MH$^+$); HRMS (FAB) Calcd. for $C_{22}H_{32}N_3O_7S_2$ (MH$^+$): 514.1682, Found: 514.1693.

EXAMPLE 6

N-(5-{2-[1-(4-Butoxy-benzenesulfonyl)-pyrrolidin-3-ylamino]-1-hydroxy-ethyl}-2-hydroxy-phenyl)-methanesulfonamide A solution of N-[2-benzyloxy-5-((1R)-2-iodo-1-triethylsilanyloxy-ethyl)-phenyl]-methanesulfonamide (0.34 g, 0.6 mmol), benzyl-[1-(4-butoxy-benzenesulfonyl)-pyrrolidin-3-yl]-amine (0.19 g, 0.5 mmol), and diisopropylethylamine (0.2 g, 1.6 mmol) in N,N'-dimethylpropyleneurea (0.5 ml) was heated at 100° C. for 3 days. It was then cooled to room temperature and treated with water. The resulting suspension was filtered, and the precipitate was chromatographed on silica gel (ethyl acetate-hexanes/1:1) to give 0.11 g of an off-white solid. 40 mg of the material obtained was dissolved in methanol (2 ml) and treated with ammonium formate (57 mg, 0.9 mmol), and 9 mg of 10% Pd/C. The mixture was stirred at reflux for 18 h. After cooling to room temperature, it was filtered through Celite. The solvent was evaporated and the residue triturated with ether-hexanes to give 25 mg of a beige solid; m.p. 95–98° C.; MS (ES) m/z 528.0 (MH$^+$); HRMS (FAB) Calcd. for $C_{23}H34N_3O_7S_2$ (MH$^+$): 528.1838, Found: 528.1829.

EXAMPLE 7

(2S)-1-[1-(4-Butoxy-benzenesulfonyl)-pyrrolidin-3-ylamino]-3-(9H-carbazol-4-yloxy)-propan-2-ol To a solution of 1-{Benzyl-[1-(4-butoxy-benzenesulfonyl)-pyrrolidin-3-yl]-amino}-3-(9H-carbazol-4-yloxy)-propan-2-ol (0.19 g, 0.3 mmol) in methanol (2 ml) was added ammonium formate (0.29 g, 4.5 mmol), and 45 mg of 10% Pd/C. The mixture was stirred at reflux for 18 h. After cooling to room temperature, it was filtered through Celite. The solvent was evaporated and the residue triturated with ether-hexanes to give 0.15 g of a white solid; m.p. 118–119° C.; MS (ES) m/z 538.1 (MH$^+$).

EXAMPLE 8

4-{(2S)-3-[1-(Benzo[1,2,5]thiadiazole-4-sulfonyl)-piperidin-4-ylamino]-2-hydroxy-propoxy}-1,3-dihydro-benzoimidazol-2-one The title compound was prepared from Intermediate 28 and 4-((2S)-3-amino-2-hydroxy-propoxy)-1,3-dihydro-benzoimidazol-2-one according to the reductive amination procedure of Intermediate 21 as a yellow solid; $^1$H NMR (DMSO) δ 1.18–1.28 (m, 2H), 1.79–1.90 (m, 2H), 2.42 (m, 1H), 2.54–2.58 (m, 1H), 2.65–2.80 (m, 1H), 3.16 (d, J=5.31 Hz, 1H), 3.68–3.79 (m, 1H), 3.83–3.88 (m, 3H), 3.91–3.96 (m, 1H), 4.96 (bs, 1H), 6.54 (d, J=7.8 Hz, 1H), 6.82 (t, J=8.1 Hz, 1H), 7.85 (s, 1H), 7.88 (d, J=1.5 Hz, 1H), 7.90 (s, 1H), 8.20 (dd, J=0.9 Hz, 7.2 Hz, 1H), 8.41 (dd, J=0.9 Hz, 8.7 Hz, 1H), 10.6 (s, 1H), 10.7 (s, 1H); MS (ES) mlz 505.0 (MH$^+$); HRMS for $C_{21}H_{24}N_6O_5S_2$: 504.1223

EXAMPLE 9

4-{(2S)-3-[1-(4-Butoxy-benzenesulfonyl)-piperidin-4-ylamino]-2-hydroxy-propoxy}-1,3-dihydro-benzoimidazol-2-one The title compound was prepared from Intermediate 27 and 4-((2S)-3-amino-2-hydroxy-propoxy)-1,3-dihydro-benzoimidazol-2-one according to the reductive amination procedure of Intermediate 21 according to the procedure of Example 1 as a light brown solid; $^1$H NMR (DMSO) δ 0.94 (t, J=5.4 Hz, 3H), 1.28–1.35 (m, 2 H), 1.41–1.46 (m, 2H), 1.69–1.75 (m, 2H), 1.84 (bs, 2H), 2.38 (m, 2 H), 2.67 (m, 2H), 2.57 (m, 2H), 2.67 (m, 2H), 3.80–3.89 (m, 3H), 3.94–3.96 (m, 2H), 4.04 (t, J=4.8 Hz, 2H), 4.7 (bs, 1H), 6.55–6.58 (m, 2H), 6.83 (t, J=6.0 Hz, 1H), 7.12 (d, J=6.6 Hz, 2 H), 7.62 (d, J=6.6 Hz, 2H), 10.55 (s, 1H), 10.65 (s, 1H); MS (ES) m/z 519.1 (MH$^+$); HRMS for $C_{25}H_{34}N_4O_6S$: 519.2254

EXAMPLE 10

(2S)-1-(4-Benzyloxy-phenoxy)-3-[1-(4-methoxy-benzenesulfonyl)-piperidin-4-ylamino]-propan-2-ol The title compound was prepared from Intermediate 29 and 1-amino-3-(4-benzyloxy-phenoxy)-propan-2-ol according to the reductive amination procedure of Intermediate 21 as an off-white solid; $^1$H NMR (DMSO) δ 1.23–1.34 (m, 2H), 1.79–1.91 (m, 2H), 2.27–2.45 (m, 4H), 2.58–2.59 (m, 2H), 2.61–2.63 (m, 2H), 3.73–3.83 (m, 3H), 3.84 (s, 3H), 4.92 (bs, 1H), 5.02 (s, 1H), 6.80–6.83 (m, 2H), 6.89–6.93 (m, 2H), 7.12–7.15 (m, 1 H), 7.31–7.44 (m, 5H), 7.63–7.67 (m, 2H); MS (ES) m/z 526.9 (MH$^+$); HRMS for $C_{28}H_{34}N_2O_6S$: 527.2238

EXAMPLE 11

(2S)-1-(4-Benzyloxy-phenoxy)-3-[1-(4-butoxy-benzenesulfonyl)-piperidin-4-ylamino]-propan-2-ol The title compound was prepared from Intermediate 27 and 1-amino-3-(4-benzyloxy-phenoxy)-propan-2-ol according to the reductive amination procedure of Intermediate 21 as an off-white solid; $^1$H NMR (DMSO) δ 0.93 (t, J=7.43 Hz, 3H), 1.37–1.49 (m, 4H), 1.66–1.76 (m, 2H), 1.81–1.91 (m, 2H), 2.28–2.36 (m, 3H), 2.59–2.63 (m, 3H), 2.73–2.77 (m, 2H), 3.75–3.85 (m, 4H), 4.05 (t, J=6.42 Hz, 2H), 5.03 (bs, 1H), 6.81–6.86 (m, 2H), 6.90–6.94 (m, 2H), 7.13 (d, J=8.91 Hz, 2H), 7.28–7.44 (m, 5H), 7.63 (d, J=8.85 Hz, 2H); MS (ES) m/z 569.0 (MH$^+$); HRMS for $C_{31}H_{40}N_2O_6S$: 569.2679

EXAMPLE 12

4-{(2S)-2-Hydroxy-3-[1-(4-methoxy-benzenesulfonyl)-piperidin-4-ylamino]-propoxy}-phenol The title compound was prepared from Intermediate 29 and 4-((2S)-3-amino-2-hydroxy-propoxy)-phenol according to the reductive amination procedure of Intermediate 21 as an off-white solid; $^1$H NMR (DMSO) δ 1.23–1.34 (m, 2H), 1.81–1.84 (m, 2H), 2.36–2.44 (m, 4H), 2.63–2.73 (m, 2H), 3.42 (m, 2H), 3.74–3.78 (m, 4H), 3.85 (s, 3H), 6.63–6.76 (m, 4H), 7.11–7.17 (m, 2H), 7.62–7.68 (m, 2H), 8.89 (s, 1H); MS (ES) m/z 437.0 (MH$^+$); HRMS for $C_{21}H_{28}N_2O_6S$: 437.1731

EXAMPLE 13

4-{(2S)-2-Hydroxy-3-[1-(4-methoxy-benzenesulfonyl)-piperidin-4-ylamino]-propoxy}-1,3-dihydro-benzoimidazol-2-one The title compound was prepared from Intermediate 29 and 4-((2S)-3-amino-2-hydroxy-propoxy)-1,3-dihydro-benzoimidazol-2-one according to the reductive amination procedure of Intermediate 21 as an off-white solid; $^1$H NMR (DMSO) δ 1.56 (m, 2H), 2.05 (m, 2H), 2.24–2.32 (m, 4H), 3.16 (d, J=5.31 Hz, 2H), 3.64 (m, 2H), 3.85 (s, 3H), 3.99 (m, 1H), 4.08–4.13 (m, 2H), 5.6 (bs, 1 H), 6.55–6.62 (m, 2H), 6.83–6.89 (m, 1 H), 7.16 (d, J=8.85 Hz, 2H), 7.68(d, J=8.85 Hz, 2H), 7.98 (s, 1H), 8.16 (s, 1H); MS (ES) m/z: 476.9 (MH$^+$); HRMS for $C_{22}H_{28}N_4O_5S$ 477.1773

EXAMPLE 14

(2S)-1-[1-(4-Butoxy-benzenesulfonyl)-piperidin-4-ylamino]-3-(9H-carbazol-4-yloxy)-propan-2-ol The title compound was prepared from Intermediate 27 and 1-amino-3-(9H-carbazol-4-yloxy)-propan-2-ol according to the reductive amination procedure of Intermediate 21 as an off-white solid; $^1$H NMR (DMSO) δ 0.90–0.96 (m, 3H), 1.30–1.50 (m, 2H), 1.65–1.77 (m, 2H), 1.81–1.91 (m, 2H), 2.34–2.46 (m, 2H), 2.64–2.71 (m, 3H), 2.78–2.84 (m, 2H), 3.07–3.12 (m, 2H), 3.47–3.53 (m, 2H), 4.00–4.08 (m, 2H), 4.10–4.14 (m, 2H), 5.08 (bs, 1H), 6.64 (d, J=7.89 Hz, 1H), 7.04–7.15 (m, 4H), 7.25–7.35 (m 2H), 7.44 (d, J=8.01 Hz, 1H), 7.59–7.66 (m, 2H), 8.16 (d, J=7.71 Hz, 1 H), 11.2 (s, 1 H); MS (ES) m/z: 552.1 (MH$^+$); HRMS for $C_{30}H_{37}N_3O_5S$ : 552.2552

EXAMPLE 15

(2S)-1-(9H-Carbazol-4-yloxy)-3-[1-(4-methoxy-benzenesulfonyl)-piperidin-4-ylamino]-propan-2-ol The title compound was prepared from Intermediate 29 and 1-amino-3-(9H-carbazol-4-yloxy)-propan-2-ol according to the reductive amination procedure of Intermediate 21 as an off-white solid; $^1$H NMR (DMSO) δ 1.30–1.46 (m, 2H), 1.67–1.72 (m, 2H), 2.34–2.45 (m, 2H), 2.64–2.72 (m, 2H), 2.80–2.83 (m, 2H), 3.16 (d, J=5.43 Hz, 1H), 3.84 (s, 3H),3.99–4.06 (m, 2H), 4.09–4.13 (m, 2H), 5.09 (bs, 1H), 6.64 (d, J=7.92 Hz, 1H), 7.04–7.15 (m, 4H), 7.25–7.35 (m, 2H), 7.43 (d, J=8.04 Hz, 1H), 7.59–7.65 (m, 2H), 8.24 (d, J=7.59 Hz, 1H), 11.2 (s, 1H); MS (ES) m/z 510.0 (MH$^+$); HRMS for $C_{27}H_{31}N_3O_5S$: 510.2094

EXAMPLE 16

(2S)-1-(9H-Carbazol-4-yloxy)-3-{1-[4-(1,1-dimethyl-propyl)-benzenesulfonyl]-piperidin-4-ylamino}-propan-2-ol The title compound was prepared from 4-(1,1-dimethyl-propyl)-benzenesulfonyl-piperidin-4-one and 1-amino-3-(9H-carbazol-4-yloxy)-propan-2-ol according to the reductive amination procedure of Intermediate 21 as an off-white solid; $^1$H NMR (DMSO) δ 0.55–0.63 )m, 3H), 1.27 (d, J=6.9 Hz, 6 H), 1.40–1.46 (m, 2H), 1.58–1.65 (m, 2H), 1.81(m, 2H), 2.38–2.45 (m, 2H), 2.63–2.82 (m, 2H), 3.07–3.13 (m, 2H), 3.51–3.54 (m, 1H), 3.90 (m, 1H), 4.08–4.13 (m, 2H), 4.66 (d, J=3.78 Hz, 1H), 5.07 (bs, 1H), 6.64 (d, J=7.95 Hz, 1H), 7.04–7.11 (m, 2H), 7.20–7.35 (m, 2H), 7.43 (d, J=8.07 Hz, 1H), 7.54–7.67 (m, 4H), 8.15 (d, J=7.71 Hz, 1H), 11.25 (s, 1H); MS (ES) m/z : 550.1 (MH$^+$); HRMS for $C_{31}H_{39}N_3O_4S$: 550.2751

EXAMPLE 17

3-{2-[1-(4-Butoxy-benzenesulfonyl)-piperidin-4-ylamino]-1-hydroxy-ethyl}-phenol The title compound was prepared from Intermediate 27 and norphenylephrine according to the reductive amination procedure of Intermediate 21 as an off-white solid; $^1$H NMR (DMSO) δ 0.93 (t, J=7.29 Hz, 3H), 1.23–1.32 (m, 2H), 1.37–1.50 (m, 2H), 1.67–1.76 (m, 2H), 1.81–1.85 (m, 2H), 2.27–2.39 (m, 4H), 2.53–2.55 (m, 1H), 2.72–2.73 (m, 1H), 3.37–3.47 (m, 1H), 4.06 (t, J=6.42 Hz, 2H), 4.41–4.45 (m, 2H), 5.12 (bs, 1H), 6.56–6.60 (m, 1H), 6.67–6.72 (m, 2 H), 7.05 (t, J=7.77 Hz, 1H), 7.10–7.16 (m, 2H), 7.60–7.66 (m, 2H), 9.25 (s, 1 H); MS (ES) m/z 449.0 (MH$^+$); HRMS for $C_{23}H_{32}N_2O_5S$: 449.2125

EXAMPLE 18

3-{1-Hydroxy-2-[1-(4-methoxy-benzenesulfonyl)-piperidin-4-ylamino]-ethyl}-phenol The title compound was prepared from Intermediate 29 and norphenylephrine according to the reductive amination procedure of Intermediate 21 as an off-white solid; $^1$H NMR (DMSO) δ 1.23–1.32 (m, 2H), 1.78–1.88 (m, 2H), 2.27–2.38 (m, 4H), 2.54–2.64 (m, 1H), 3.39–3.44 (m, 2H), 3.85 (s, 3H), 4.43–4.48 (m, 2H), 5.33 (bs, 1 H), 6.57–6.61 (m, 1H), 6.68–6.72 (m, 2H), 7.06 (t, J=7.77 Hz, 1H), 7.12–7.17 (m, 2H), 7.63–7.68 (m, 2H), 9.26 (s, 1 H); MS (ES) m/z 407.0 (MH$^+$); HRMS for $C_{23}H_{27}N_3O_4S_2$: 407.1656

EXAMPLE 19

3-(2-{1-[4-(1,1-Dimethyl-propyl)-benzenesulfonyl]-piperidin-4-ylamino}-1-hydroxy-ethyl)-phenol The title compound was prepared from 4-(1,1-dimethyl-propyl)-benzenesulfonyl-piperidin-4-one and norphenylephrine according to the reductive amination procedure of Intermediate 21 as an off-white solid; $^1$H NMR (DMSO) δ 0.60 (t, J=7.32 Hz, 3H), 1.28 (s, 6H), 1.60–1.68 (m, 2H), 1.77–1.91 (m, 2H), 2.27–2.45 (m, 4H), 2.51–2.56 (m, 2H), 2.56–2.59 (m, 2H), 3.42–3.47 (m, 2H), 4.42–4.44 (m, 2H), 5.18 (bs, 1H), 6.57–6.60 (m, 1H), 6.67–6.71 (m, 2H), 7.05 (t, J=7.74 Hz, 1H), 7.58 (d, J=8.61 Hz, 2H), 7.65 (d, J=8.58 Hz, 2H) 9.25 (s, 1H); MS (ES) m/z 446.9 (MH$^+$); HRMS for $C_{24}H_{34}N_2O_4S$: 447.2323

EXAMPLE 20

4-{(2S)-3-[1-(3,4-Dimethoxy-benzenesulfonyl)-piperidin-4-ylamino]-2-hydroxy-propoxy}-1,3-dihydro-benzoimidazol-2-one The title compound was prepared from Intermediate 30 and 4-((2S)-3-amino-2-hydroxy-propoxy)-1,3-dihydro-benzoimidazol-2-one according to the reductive amination procedure of Intermediate 21 as an off-white solid; $^1$H NMR (DMSO) δ 1.40 (m, 2H), 1.92 (m, 4H), 2.33–2.41 (m, 2H), 2.73 (m, 1H), 2.83 (m, 1H), 3.53–3.65 (m, 3H), 3.84 (d, J=4.89 Hz, 6 H), 3.90–3.98 (m, 3H), 6.55–6.60 (m, 2H), 6.84 (t, J=8.04 Hz, 1H), 7.14–7.19 (m, 2H), 7.30 (dd, J=1.92 Hz, 8.43 Hz, 1H), 10.55 (s, 1H), 10.65 (s, 1H); MS (ES) m/z 507.0 (MH$^+$); HRMS for $C_{23}H_{30}N_4O_7S$: 507.1953

EXAMPLE 21

(2S)-1-(9H-Carbazol-4-yloxy)-3-[1-(3,4-dimethoxy-benzenesulfonyl)-piperidin-4-ylamino]-propan-2-ol The title compound was prepared from Intermediate 30 and 1-amino-3-(9H-carbazol-4-yloxy)-propan-2-ol according to the reductive amination procedure of Intermediate 21 as an off-white solid; $^1$H NMR (DMSO) δ 1.29–1.40 (m, 2H), 1.84–1.91 (m, 2H), 2.37–2.43 (m, 3H), 2.65–2.72 (m, 1H), 2.82 (m, 1H), 3.39–3.45 (m, 2H), 3.82 (d, J=6.09 Hz, 6 H), 4.01–4.06 (m, 1H), 4.09–4.11 (m, 2H), 5.06 (bs, 1H), 5.76 (s, 1H), 6.64 (d, J=7.92 Hz, 1H), 7.03–7.16 (m, 4H), 7.24–7.35 (m, 3H), 7.43 (d, J=8.13 Hz, 1H), 8.16 (d, J=7.64 Hz, 1H), 11.2 (s, 1H); MS (ES) m/z 540.0 (MH$^+$); HRMS for $C_{28}H_{33}N_3O_6S$: 540.2184

EXAMPLE 22

4-{3-[1-(4-Butoxy-benzenesulfonyl)-piperidin-4-ylamino]-2-hydroxy-propoxy}-phenol The title compound was prepared from Intermediate 27 and 4-((2S)-3-amino-2-hydroxy-propoxy)-phenol according to the reductive amination procedure of Intermediate 21 as a white solid; $^1$H NMR (DMSO) δ 0.936 (t, J=7.29 Hz, 3H), 1.23–1.30 (m, 2H), 1.37–1.50 (m, 2H), 1.67–1.76 (m, 2H), 1.79–1.83 (m, 2H), 2.22–2.27 (m, 1H), 2.34–2.41 (m, 4H), 2.59–2.63 (m, 2H), 2.72–2.73 (m, 1H), 3.46–3.54 (m, 1H), 3.69–3.78 (m, 2H), 4.05–4.09 (m, 2H), 4.89 (bs, 1H), 6.62–6.79 (m, 4H), 7.13 (d, J=8.88 Hz, 2H), 7.61–7.65 (m, 2H), 8.88 (s, 1H); MS (ES) m/z 479.0 (MH$^+$); HRMS for $C_{24}H_{34}N_2O_6S$: 479.2217

EXAMPLE 23

N-(5-{2-(1-(Dibenzofuran-2-sulfonyl)-piperidin-4-ylamino]-1-hydroxy-ethyl}-2-hydroxy-phenyl)-methanesulfonamide The title compound was prepared from Intermediate 31 and N-[5-(2-amino-1-hydroxy-ethyl)-2-hydroxy-phenyl]-methanesulfonamide according to the reductive amination procedure of Intermediate 21 as an orange solid; $^1$H NMR (DMSO) d 1.23–1.37 (m, 2H), 1.80–1.91 (m, 2H), 2.39–2.59 (m, 5H), 2.89 (s, 3H), 3.51–3.56 (m, 4H), 4.39–4.43 (m, 2H), 5.41 (bs, 1H), 6.75 (d, J=11.25 Hz, 1H), 6.94 (dd, J=2.01 Hz, 6.3 Hz, 1H), 7.11 (d, J=1.98 Hz, 1H), 7.46–7.51 (m, 1H), 7.60–7.66 (m, 1H), 7.80 (d, J=8.25 Hz, 1H), 7.87 (q, J=1.86 Hz, 1H), 7.96 (d, J=3.54 Hz, 1H), 8.38 (d, J=7.11 Hz, 1H), 8.64 (d, J=1.71 Hz, 1H); MS (ES) m/z 560.0 (MH$^+$); HRMS for $C_{26}H_{29}N_3O_7S_2$: 560.1521.

EXAMPLE 24

4-{3-[1-(Dibenzofuran-2-sulfonyl)-piperidin-4-ylamino]-(2S)-2-hydroxy-propoxy}-1,3-dihydro-benzoimidazol-2-one The title compound was prepared from Intermediate 31 and 4-((2S)-3-amino-2-hydroxy-propoxy)-1,3-dihydro-benzoimidazol-2-one according to the reductive amination procedure of Intermediate 21 as an off white solid; $^1$H NMR (DMSO) 61.33-1.40 (m, 2H), 1.85–1.89 (m, 2H), 2.43–2.47 (m, 3H), 2.54–2.59 (m, 1H), 2.67–2.71 (m, 1H), 3.49–3.53 (m, 2H), 3.79–3.95 (m, 4H), 4.85 (bs, 1H), 6.53 (d, J=8.1 Hz, 1H), 6.79 (t, J=8.1 Hz, 1H), 7.46–7.52 (m, 1H), 7.60–7.66 (m, 1H), 7.80 (d, J=8.1 Hz, 1H), 7.86 (dd, J=1.8 Hz, 6.9 Hz, 1H), 7.95 (d, J=8.7 Hz, 1H), 8.38 (d, J=7.2 Hz, 1H), 8.64 (d, J=1.8 Hz, 1H), 10.56 (s, 1H), 10.63 (s, 1H); MS (ES) m/z 536.9 (MH$^+$); HRMS for $C_{27}H_{28}N_4O_6S$: 537.1806.

EXAMPLE 25

1-Hexyl-3-(4-{4-[(2S)-2-hydroxy-3-(4-hydroxy-phenoxy)-propylamino]-piperidine-1-sulfonyl}-phenyl)-urea The title compound was prepared from Intermediate 32 and 4-((2S)-3-amino-2-hydroxy-propoxy)-phenol according to the reductive amination procedure of Intermediate 21 as a beige solid; $^1$H NMR (DMSO) δ 0.84–0.89 (m, 3H), 1.38–1.45 (m, 2H), 1.79–1.84 (m, 2H), 2.22–2.38 (m, 4H), 2.37–2.48 (m, 2H), 2.60–2.66 (m, 2H), 2.75 (s, 1H), 2.89 (s, 1H), 3.08 (q, 2H), 3.33–3.41 (m, 6H), 3.69–3.87 (m, 4H), 4.89 (bs, 1H), 6.34 (t, J=5.55 Hz, 1H), 6.54–6.78 (m, 4H), 7.53–7.62 (m, 3H), 8.88 (bs, 1H), 8.99 (s, 1H); MS (ES) m/z 549.1 (MH$^+$); HRMS for $C_{27}H_{40}N_4O_6S$: 549.2742.

EXAMPLE 26

N-[5-(2-{1-[4-(3-Hexyl-ureido)-benzenesulfonyl]-piperidin-4-ylamino}-1-hydroxy-ethyl)-2-hydroxy-phenyl]-methanesulfonamide The title compound was prepared from Intermediate 32 and N-[5-((1R)-2-amino-1-hydroxy-ethyl)-2-hydroxy-phenyl]-methanesulfonamide according to the reductive amination procedure of Intermediate 21 as an off-white solid; $^1$H NMR (DMSO) δ 0.84–0.89 (m, 3H), 1.38–1.45 (m, 2H), 1.77–1.85 (m, 2H), 2.09 (s, 1H), 2.22–2.41 (m, 4H), 2.53–2.63 (m, 4H), 2.72–2.74 (m, 2H), 2.90 (s, 1H), 3.04–3.13 (m, 2H), 3.16 (s, 1H), 3.42 (m, 4H), 4.40–4.45 (m, 2H), 5.16 (bs, 1H), 6.33 (t, J=5.58 Hz, 1H), 6.79 (d, J=8.25 Hz, 1H), 6.96 (dd, J=1.98 Hz, 6.33 Hz, 1H), 7.13 (d, J=1.95 Hz, 1H), 7.53–7.62 (m, 3H), 8.96 (s, 1H); MS (ES) m/z 612.0 (MH$^+$); HRMS for $C_{27}H_{41}N_5O_7S_2$: 612.2519.

EXAMPLE 27

1-Hexyl-3-(4-{4-[(2S)-2-hydroxy-3-(2-oxo-2,3-dihydro-1H-benzoimidazol-4-yloxy)-propylamino]-piperidine-1-sulfonyl}-phenyl)-urea The title compound was prepared from Intermediate 32 and 4-((2S)-3-amino-2-hydroxy-propoxy)-1,3-dihydro-benzoimidazol-2-one according to the reductive amination procedure of Intermediate 21 as a tan foam; $^1$H NMR (DMSO) δ 0.84–0.89 (m, 3H), 1.32–1.45 (m, 4H), 1.71–1.91 (m, 2H), 2.32–2.39 (m, 4H), 2.55–2.59 (m, 2H), 2.69–2.73 (m, 2H), 3.02–3.11 (m, 2H), 3.36–3.40 (m, 4H), 3.81–3.89 (m, 4H), 3.93–3.98 (m, 2H), 4.84 (bs, 1H), 6.32 (t, J=5.64 Hz, 1H), 6.56 (q, J=4.08 Hz, 2H), 6.83 (t, J=8.07 Hz, 1H), 7.53–7.66 (m, 3H), 8.95 (s, 1H), 10.55 (s, 1H), 10.65 (s, 1H); MS (ES) m/z 589.1 (MH$^+$); HRMS for $C_{28}H_{40}N_6O_6S$: 589.2800.

EXAMPLE 28

5-(4-{4-[(2S)-2-Hydroxy-3-(2-oxo-2,3-dihydro-1H-benzoimidazol-4-yloxy)-propylamino]-piperidine-1-sulfonyl}-benzyl)-thiazolidine-2,4-dione The title compound was prepared from 5-[4-(4-oxo-piperidine-1-sulfonyl)-benzyl]-thiazolidine-2,4-dione and (S)-4-[2-hydroxy-3-aminopropoxy]-1,3-dihydro-2H-benzimidazol-2-one according to the reductive amination procedure of Intermediate 21 as a pale grey solid; 1H NMR (300 MHz, DMSO-d6): δ 1.20–1.40 (m, 2 H), 1.80–2.00 (m, 2 H), 2.30–4.00 (m, 12 H), 4.65 (dd, J=8.0, 3.5 Hz, 1 H), 6.56 (d, J=3.2 Hz, 1 H), 6.59 (d, J=3.8 Hz, 1 H), 6.85 (t, J=3.5 Hz, 1 H), 7.50 (d, J=8.1 Hz, 2 H), 7.66 (d, J=8.1 Hz, 2 H), 10.70 (s, 1 H), 10.79 (brs, 1 H); MS (ES) m/z : 576.0 (M$^+$+H); HRMS Calcd. for C25H30N5O7S2 (M$^+$+H): 576.1587. Found: 576.1596.

EXAMPLE 29

N-[5-(2-{1-[4-(2,4-Dioxo-thiazolidin-ylmethyl)-benzenesulfonyl]-piperidin-4-ylamino}-(1R)-1-hydroxy-ethyl)-2-hydroxy-phenyl]-methanesulfonamide The title compound was prepared from 5-[4-(4-oxo-piperidine-1-sulfonyl)-benzyl]-thiazolidine-2,4-dione and (R)-N-[5-(2-amino-1-hydroxy-ethyl)-2-hydroxy-phenyl}-methanesulfonamide according to the reductive amination procedure of Intermediate 21 as an off-white solid; 1H NMR (300 MHz, DMSO-d6): δ 1.20–1.40 (m, 2 H), 1.80–2.00 (m, 2 H), 2.25–2.50 (m, 2 H), 2.60–2.90 (m, 3 H), 2.91 (s, 3 H), 3.00–3.40 (m, 2 H), 3.55–3.75 (m, 2 H), 4.55–4.70 (m, 2 H), 6.83 (d, J=8.3 Hz, 1 H), 7.01 (dd, J=8.3, 1.7 Hz, 1 H), 7.17 (d, J=1.7 Hz, 1 H), 7.50 (d, J=8.3 Hz, 2 H), 7.65 (d, J=8.3 Hz, 2 H); MS (ES) m/z: 598.9 (M$^+$+H); HRMS Calcd. for C24H31N4O8S3 (M++H): 599.1304. Found: 599.1267.

What is claimed is:
1. A compound of formula I having the structure

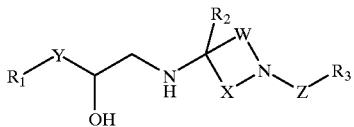

I wherein:

W is $(CH_2)_m$;
X is $(CH_2)_n$;
Y is $OCH_2$, $SCH_2$, or a bond;
Z is $SO_2$, CO, or P(O)OR;
R is alkyl or aryl;
$R_1$ is phenyl substituted with $R_4$ and $R_5$, or Het substituted with $R_4$ and $R_5$;
Het is selected from the group of pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;
$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;
$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —NHCOR$_7$, —NR$_8$R$_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms $R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —NR$_8$R$_9$, or —NR$_9$(CH$_2$)$_p$—R$_8$ $R_8$ is hydrogen, alkoxy of 1–6 carbon atoms, alkyl of 1–6 carbon atoms, hydroxy, —(CH$_2$)$_p$—COR$_9$, or —(CH$_2$)$_p$—R$_9$;

R$_9$ is hydrogen, hydroxy, alkyl of 1–6 carbon atoms, alkoxy of 1–6 carbon atoms, or —NR$_{10}$R$_{10}$;

R$_{10}$ is hydrogen, alkyl of 1–6 carbon atoms, aryl, or Het;

m+n=4 p is 0–6;

or a pharmaceutically acceptable salt thereof.

2. The compound according to claim 1, wherein

R$_2$ is hydrogen;

R$_3$ is alkyl of 1–6 carbon atoms, cycloalkyl of 4–8 carbon atoms, aryl substituted with R$_4$ and R$_5$, or Het substituted with R$_4$ and R$_5$;

R$_4$ and R$_5$ are each, independently, hydrogen, alkyl of 1–6 carbon atoms, halogen, alkoxy of 1–6 carbon atoms, arylalkoxy having 1–6 carbon atoms in the alkyl chain, hydroxy, arylalkyl having 1–6 carbon atoms in the alkyl chain, Het-alkyl having 1–6 carbon atoms in the alkyl chain, —NHCOR$_7$, —NHSO$_2$R$_7$, —NR$_8$R$_8$, or —COR$_8$;

Het is selected from the group of pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;

or a pharmaceutically acceptable salt thereof.

3. The compound of claim 2, wherein

Y is OCH$_2$ or a bond;

Z is SO$_2$;

R$_2$ is hydrogen;

R$_3$ is phenyl substituted with R$_4$ and R$_5$, or Het substituted with R$_4$ and R$_5$;

R$_4$ and R$_5$ are each, independently, hydrogen, alkyl of 1–6 carbon atoms, alkoxy of 1–6 carbon atoms; arylalkyl having 1–6 carbon atoms in the alkyl chain, Het-alkyl having 1–6 carbon atoms in the alkyl chain, —NHCOR$_7$, —NHSO$_2$R$_7$, or —NR$_8$R$_8$;

R$_7$ is alkyl of 1–6 carbon atoms, —NR$_8$R$_9$, or —NR$_9$(CH$_2$)$_p$—R$_8$;

R$_8$ is —(CH$_2$)$_p$—COR$_9$, or —(CH$_2$)$_p$—R$_9$;

R$_9$ is alkoxy of 1–6 carbon atoms or —NR$_{10}$R$_{10}$;

R$_{10}$ is hydrogen or alkyl of 1–6 carbon atoms;

Het is pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;

or a pharmaceutically acceptable salt thereof.

4. The compound of claim 1, which is a) 4-{(2S)-3-[1-(Benzo[1,2,5]thiadiazole-4-sulfonyl)-piperidin-4-ylamino]-2-hydroxy-propoxy}-1,3-dihydro-benzoimidazol-2-one;

b) (2S)-1-(4-Benzyloxy-phenoxy)-3-[1-(4-methoxy-benzenesulfonyl)-piperidin-4-ylamino]-propan-2-ol;

c) (2S)-1-(4-Benzyloxy-phenoxy)-3-[1-(4-butoxy-benzenesulfonyl)-piperidin-4-ylamino]-propan-2-ol;

d) 4-{3-[1-(4-Butoxy-benzenesulfonyl)-piperidin-4-ylamino]-2-hydroxy-propoxy}-phenol e) 4-{(2S)-2-Hydroxy-3-[1-(4-methoxy-benzenesulfonyl)-piperidin-4-ylamino]-propoxy}-phenol;

f) 4-{(2S)-2-Hydroxy-3-[1-(4-methoxy-benzenesulfonyl)-piperidin-4-ylamino]-propoxy}-1,3-dihydro-benzoimidazol-2-one;

g) (2S)-1-(9H-Carbazol-4-yloxy)-3-[1-(4-methoxy-benzenesulfonyl)-piperidin-4-ylamino]-propan-2-ol;

h) (2S)-1-[1-(4-Butoxy-benzenesulfonyl)-piperidin-4-ylamino]-3-(9H-carbazol-4-yloxy)-propan-2-ol;

i) (2S)-1-(9H-Carbazol-4-yloxy)-3-{1-[4-(1,1-dimethyl-propyl)-benzenesulfonyl]-piperidin-4-ylamino}-propan-2-ol;

j) 3-{1-Hydroxy-2-[1-(4-methoxy-benzenesulfonyl)-piperidin-4-ylamino]-ethyl}-phenol;

k) 3-{2-[1-(4-Butoxy-benzenesulfonyl)-piperidin-4-ylamino]-1-hydroxy-ethyl}-phenol;

l) 3-(2-{1-[4-(1,1-Dimethyl-propyl)-benzenesulfonyl]-piperidin-4-ylamino}-1-hydroxy-ethyl)-phenol;

m) (2S)-1-(9H-Carbazol-4-yloxy)-3-[1-(3,4-dimethoxy-benzenesulfonyl)-piperidin-4-ylamino]-propan-2-ol;

n) 4-{(2S)-3-[1-(3,4-Dimethoxy-benzenesulfonyl)-piperidin-4-ylamino]-2-hydroxy-propoxy}-1,3-dihydro-benzoimidazol-2-one;

o) 5-(4-{4-[2-Hydroxy-3-(2-oxo-2,3-dihydro-1H-benzoimidazol-4-yloxy)-propylamino]-piperidine-1-sulfonyl}-benzyl)-thiazolidine-2,4-dione;

p) N-[5-(2-{1-[4-(2,4-Dioxo-thiazolidin-5-ylmethyl)-benzenesulfonyl]-piperidin-4-ylamino}-1-hydroxy-ethyl)-2-hydroxy-phenyl]-methanesulfonamid;

q) 4-{3-[1-(Dibenzofuran-2-sulfonyl)-piperidin-4-ylamino]-2-hydroxy-propoxy-1,3-dihydro-benzoimidazol-2-one;

r) N-(5-{2-[1-(Dibenzofuran-2-sulfonyl)-piperidin-4-ylamino]-1-hydroxy-ethyl}-2-hydroxy-phenyl)-methanesulfonamide;

s) 1-Hexyl-3-(4-{4-[(2S)-2-hydroxy-3-(4-hydroxy-phenoxy)-propylamino]-piperidine-1-sulfonyl}-phenyl)-urea;

t) 1-Hexyl-3-(4-{4-[2-hydroxy-3-(2-oxo-2,3-dihydro-1H-benzoimidazol-4-yloxy)-propylamino]-piperidine-1-sulfonyl}-phenyl)-urea; or u) N-[5-(2-{1-[4-(3-Hexyl-ureido)-benzenesulfonyl]-piperidin-4-ylamino}-1-hydroxy-ethyl)-2-hydroxy-phenyl]-methanesulfonamide;

or a pharmaceutically acceptable salt thereof.

5. A method of treating metabolic disorders mediated by insulin resistance or hyperglycemia in a mammal in need thereof which comprises providing to said mammal, an effective amount of a compound of formula I having the structure

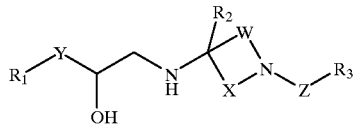

wherein:
W is $(CH_2)_m$;
X is $(CH_2)_n$;
Y is $OCH_2$, $SCH_2$, or a bond;
Z is $SO_2$, CO, or P(O)OR;
R is alkyl or aryl;
$R_1$ is phenyl substituted with $R_4$ and $R_5$, or Het substituted with $R_4$ and $R_5$;
$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;
$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —$NHCOR_7$, —$NR_8R_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;
$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —$NHCOR_7$, —$NHSO_2R_7$, —$NHP(O)(R_7)_2$, —$COR_8$, —$SO_2R_8$, —$NR_8R_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms
$R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —$NR_8R_9$, or —$NR_9(CH_2)_p$—$R_8$
$R_8$ is hydrogen, alkoxy of 1–6 carbon atoms, alkyl of 1–6 carbon atoms, hydroxy, —$(CH_2)_p$—$COR_9$, or —$(CH_2)_p$—$R_9$;
$R_9$ is hydrogen, hydroxy, alkyl of 1–6 carbon atoms, alkoxy of 1–6 carbon atoms, or —$NR_{10}R_{10}$;
$R_{10}$ is hydrogen, alkyl of 1–6 carbon atoms, aryl, or Het;
Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;
m+n=4;
p is 0–6;
or a pharmaceutically acceptable salt thereof.
6. A method of treating or inhibiting type II diabetes in a mammal in need thereof which comprises providing to said mammal, an effective amount of a compound of Formula I having the structure

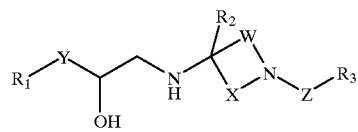

wherein
W is $(CH_2)_m$;
X is $(CH_2)_n$;
Y is $OCH_2$, $SCH_2$, or a bond;
Z is $SO_2$, CO, or P(O)OR;
R is alkyl or aryl;
$R_1$ is phenyl substituted with $R_4$ and $R_5$, or Het substituted with $R_4$ and $R_5$;
$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;
$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —$NHCOR_7$, —$NR_8R_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms $R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —NR$_8$R$_9$, or —NR$_9$(CH$_2$)$_p$—R$_8$ $R_8$ is hydrogen, alkoxy of 1–6 carbon atoms, alkyl of 1–6 carbon atoms, hydroxy, —(CH$_2$)$_p$—COR$_9$, or —(CH$_2$)$_p$—R$_9$;

$R_9$ is hydrogen, hydroxy, alkyl of 1–6 carbon atoms, alkoxy of 1–6 carbon atoms, or —NR$_{10}$R$_{10}$;

$R_{10}$ is hydrogen, alkyl of 1–6 carbon atoms, aryl, or Het;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m+n=4;

p is 0–6;

or a pharmaceutically acceptable salt thereof.

7. A method of modulating glucose levels in a mammal in need thereof which comprises providing to said mammal, an effective amount of a compound of formula I having the structure

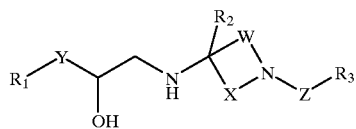

wherein:
W is (CH$_2$)$_m$;
X is (CH$_2$)$_n$;
Y is OCH$_2$, SCH$_2$, or a bond;
Z is SO$_2$, CO, or P(O)OR;
R is alkyl or aryl;
$R_1$ is phenyl substituted with $R_4$ and $R_5$, or Het substituted with $R_4$ and $R_5$;
$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;
$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —NHCOR$_7$, —NR$_8$R$_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms $R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —$NR_8R_9$, or —$NR_9(CH_2)_p$—$R_8$ $R_8$ is hydrogen, alkoxy of 1–6 carbon atoms, alkyl of 1–6 carbon atoms, hydroxy, —$(CH_2)_p$—$COR_9$, or —$(CH_2)_p$—$R_9$;

$R_9$ is hydrogen, hydroxy, alkyl of 1–6 carbon atoms, alkoxy of 1–6 carbon atoms, or —$NR_{10}R_{10}$;

$R_{10}$ is hydrogen, alkyl of 1–6 carbon atoms, aryl, or Het;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m+n=4;

p is 0–6;

or a pharmaceutically acceptable salt thereof.

8. A method of increasing the lean meat to fat ratio in a mammal in need thereof, which comprises providing to said mammal an effective amount of a compound of formula I having the structure

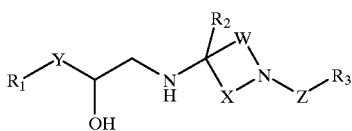

I wherein:

W is $(CH_2)_m$;

X is $(CH_2)_n$;

Y is $OCH_2$, $SCH_2$, or a bond;

Z is $SO_2$, CO, or P(O)OR;

R is alkyl or aryl;

$R_1$ is phenyl substituted with $R_4$ and $R_5$, or Het substituted with $R_4$ and $R_5$;

$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;

$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —$NHCOR_7$, —$NR_8R_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl having 1–6 carbon atoms in the alkyl chain, phosphonylalkyl of 1–6 carbon atoms, or phosphorylalkyl of 1–6 carbon atoms;

$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —$NHCOR_7$, —$NHSO_2R_7$, —$NHP(O)(R_7)_2$, —$COR_8$, —$SO_2R_8$, —$NR_8R_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms $R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —$NR_8R_9$, or —$NR_9(CH_2)_p$—$R_8$ $R_8$ is hydrogen, alkoxy of 1–6 carbon atoms, alkyl of 1–6 carbon atoms, hydroxy, —$(CH_2)_p$—$COR_9$, or —$(CH_2)_p$—$R_9$;

$R_9$ is hydrogen, hydroxy, alkyl of 1–6 carbon atoms, alkoxy of 1–6 carbon atoms, or —$NR_{10}R_{10}$;

$R_{10}$ is hydrogen, alkyl of 1–6 carbon atoms, aryl, or Het;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m+n=4;

p is 0–6;

or a pharmaceutically acceptable salt thereof.

9. A pharmaceutical composition which comprises a compound of formula I having the structure

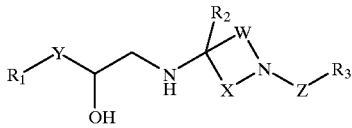

wherein:

W is $(CH_2)_m$;

X is $(CH_2)_n$;

Y is $OCH_2$, $SCH_2$, or a bond;

Z is $SO_2$, CO, or P(O)OR;

R is alkyl or aryl;

$R_1$ is phenyl substituted with $R_4$ and $R_5$, or Het substituted with $R_4$ and $R_5$;

$R_2$ is hydrogen, trifluoromethyl, alkyl of 1–6 carbon atoms, alkenyl of 2–7 carbon atoms, alkynyl of 2–7 carbon atoms or cycloalkyl of 4–8 carbon atoms;

$R_3$ is alkyl of 1–6 carbon atoms, alkenyl of 2–7 carbon atoms, alkynyl of 2–7 carbon atoms, cycloalkyl of 4–8 carbon atoms, aryl substituted with $R_4$ and $R_5$, Het substituted with $R_4$ and $R_5$, aryloxy, —$NHCOR_7$, —$NR_8R_8$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_4$, and $R_5$, are each, independently, hydrogen, trifluoromethyl, alkyl of 1–6 carbon atoms, alkenyl of 2–7 carbon atoms, alkynyl of 2–7 carbon atoms, cycloalkyl of 4–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —$NHCOR_7$, —$NHSO_2R_7$, —$NHP(O)(R_7)_2$, —$COR_8$, —$SO_2R_8$, —$NR_8R_8$, carboxy, alkylcarbonyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms $R_7$ is hydrogen, trifluoromethyl, alkyl of 1–6 carbon atoms, cycloalkyl of 4–8 carbon atoms, alkenyl of 2–7 carbon atoms, alkynyl of 2–7 carbon atoms, aryl, alkoxy of 1–6 carbon atoms, —$NR_8R_9$, or —$NR_9(CH_2)_p R_8$ $R_8$ is hydrogen, alkoxy of 1–6 carbon atoms, alkyl of 1–6 carbon atoms, hydroxy, —$(CH_2)_p$—$COR_9$, or —$(CH_2)_p$—$R_9$;

$R_9$ is hydrogen, hydroxy, alkyl of 1–6 carbon atoms, alkoxy of 1–6 carbon atoms, or —$NR_{10}R_{10}$;

$R_{10}$ is hydrogen, alkyl of 1–6 carbon atoms, aryl, or Het;

Het is selected from the group of pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;

m+n=4;

p is 0–6;

or a pharmaceutically acceptable salt thereof, and a pharmaceutical carrier.

* * * * *